US010036037B2

(12) United States Patent
Bowen et al.

(10) Patent No.: US 10,036,037 B2
(45) Date of Patent: Jul. 31, 2018

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Timothy D. Panosian, St. Louis, MO (US); Yong Yin, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/230,112

(22) Filed: Aug. 5, 2016

(65) Prior Publication Data
US 2017/0137842 A1    May 18, 2017

Related U.S. Application Data

(60) Provisional application No. 62/206,616, filed on Aug. 18, 2015.

(51) Int. Cl.
| A01H 5/00 | (2018.01) |
| C12N 15/82 | (2006.01) |
| C12N 15/32 | (2006.01) |
| C07K 14/325 | (2006.01) |
| C12Q 1/6895 | (2018.01) |
| G01N 33/68 | (2006.01) |
| A01N 63/02 | (2006.01) |

(52) U.S. Cl.
CPC ......... *C12N 15/8286* (2013.01); *A01N 63/02* (2013.01); *C07K 14/325* (2013.01); *C12Q 1/6895* (2013.01); *G01N 33/68* (2013.01); *C12Q 2600/13* (2013.01); *C12Q 2600/158* (2013.01); *G01N 2333/325* (2013.01)

(58) Field of Classification Search
CPC .................................................. C07K 14/325
See application file for complete search history.

(56) References Cited

U.S. PATENT DOCUMENTS

| 7,510,878 B2 | 3/2009 | Abad et al. |
| 7,772,465 B2 | 8/2010 | Abad et al. |
| 7,812,129 B1 | 10/2010 | Abad et al. |
| 8,609,936 B2 | 12/2013 | Baum et al. |
| 8,829,279 B2 | 9/2014 | Carozzi et al. |
| 2008/0172762 A1 | 7/2008 | Cerf et al. |
| 2009/0313721 A1 | 12/2009 | Abad et al. |
| 2010/0005543 A1 | 1/2010 | Sampson et al. |
| 2010/0077507 A1 | 3/2010 | Abad et al. |
| 2010/0077508 A1 | 3/2010 | Abad et al. |
| 2010/0192256 A1 | 7/2010 | Abad et al. |
| 2010/0269221 A1 | 10/2010 | Abad et al. |
| 2011/0030096 A1 | 2/2011 | Sampson et al. |
| 2011/0055968 A1 | 3/2011 | Cerf et al. |
| 2011/0112013 A1 | 5/2011 | Abad et al. |
| 2011/0154536 A1 | 6/2011 | Abad et al. |
| 2012/0047606 A1 | 2/2012 | Abad et al. |
| 2012/0117690 A1 | 5/2012 | Cerf et al. |
| 2012/0167259 A1 | 6/2012 | Liu et al. |
| 2012/0278954 A1 | 11/2012 | Bowen et al. |
| 2013/0097735 A1 | 4/2013 | Bowen et al. |
| 2013/0269060 A1 | 10/2013 | Baum et al. |
| 2016/0355842 A1* | 12/2016 | Parks ................. C12N 15/8285 |

FOREIGN PATENT DOCUMENTS

| WO | WO 2007/147096 | 12/2007 |
| WO | WO/2016/061391 A2 | 4/2016 |
| WO | WO/2016/061392 A2 | 4/2016 |

OTHER PUBLICATIONS

Tounsi et al (J. Appl. MicrobioL 95:23-28; 2003).*
De Maagd et al (Appl Environ. Microbiol 65:4369-4374, 1999).*
Aronson et al ((FEMS Microbiol. Lett. 2001, 195:1-8).*
Bravo et al (Microbial Biotechnology, 6, (2012) 17-26.*
Greyson et al (Journal of the American Oil Chemists' Society Feb. 2002, vol. 79, Issue 2, pp. 171-174).*
Invitation to Pay Additional Fees regarding International Application No. PCT/US2016/045810, dated Oct. 24, 2016.
GenBank Accession No. HG975440, dated Jun. 25, 2014.
GenBank Accession No. HG975513, dated Jun. 25, 2014.
International Search Report and Written Opinion regarding International Application No. PCT/US2016/045810, dated Jan. 6, 2017.

* cited by examiner

*Primary Examiner* — Lee A Visone
(74) *Attorney, Agent, or Firm* — Dentons US LLP; Carine M. Doyle, Esq.; T. K. Ball, Esq.

(57) ABSTRACT

Pesticidal proteins exhibiting toxic activity against Coleopteran and Lepidopteran pest species are disclosed, and include, but are not limited to, TIC2421 TIC3008, and TIC7055. DNA constructs are provided which contain a recombinant nucleic acid sequence encoding one or more of the disclosed pesticidal proteins. Transgenic plants, plant cells, seed, and plant parts resistant to Lepidopteran and Coleopteran infestation are provided which contain recombinant nucleic acid sequences encoding the pesticidal proteins of the present invention. Methods for detecting the presence of the recombinant nucleic acid sequences or the proteins of the present invention in a biological sample, and methods of controlling Coleopteran and Lepidopteran species pests using any of the TIC2421, TIC3008, and TIC7055 pesticidal proteins are also provided.

21 Claims, 2 Drawing Sheets

```
TIC3008   MKTNNQIRDRKKKIAKIVPICVISTGFLVGLVNPAFAKTTESKLSSQQTIHDQGIKSTSL
TIC7055   MKTNNQIRDGKKKLAQIVPICVLSTGFLVGLVNPAFAKTTESQVSSQQIIHDQVIKPRSL
TIC2421   MYTNNKMKCWKKKLAKVAPICVLSTGFLVGVANPAFAAS------KTPQTVHAQAKQSNLS
          * ***:  * *** *: ****:******* .*****::      ..  * **   : ::

TIC3008   ATSNDNINLYHIGDDLNQRIYDAVKNRPDLFVYHHVKGESGR-NEKISDMDKSLTNGYIV
TIC7055   ATSNDNINLDHIGDDLNQRIYDAVKNRPDLFVYHHVKEESGR-NEKISDMDKSLANGYIV
TIC2421   TTSNS---NLVHIGDDLNQRIHDAVKNKPDLFLYRYLRDDRGRTNVRMNDMPQSDNSGYNF
          :***.   **  ********:******:****:*  ::.  *  : :.:*  *.*..*:

TIC3008   VMNNLKYPGVTINNGYNIDWNQREYVGGDIKVTGKQDSVDGLHSFTLGTFHNTENIEQIA
TIC7055   VMNNLKYPGVTINNGYSIDWNQREYVGGDIKVTGKQDSVDGLHSFTLGTFHNTEDIEQIA
TIC2421   VMNSLQYGKVTINNGYNIDWNQREYVGGDIKVTGKQDSIGGLHSFTIGTFHNTEDIEQTA
          ***.*:* ********.********************::******:*******:*** *

TIC3008   TTQKESYQTTDSFTYSTSKGVKLGLTESLKATAGVPLIVNGEETTLSTEFSYNQTSSNT
TIC7055   TTQKESYQTTDSFVYSTSKGVKLGLTESLKATAGVPLIVNGEETTLSTEFSYNQTSSNT
TIC2421   TTQKETYQTTDSFTYSNSEGVKLGLTESIKATAGVPFVIAGEETTLSSEFSYNHTSSNT
          *****:*******.**.*.*********:*******::..******:*****:*****

TIC3008   ATNSHTIEFPSQTIKVKPHGTTIYIGEVKQLKFSGDYSGTTKLTTQDVSFPIVDSEGHWG
TIC7055   ATNSHTIEFPSQTIKVKPHGTTIYIGEVKQLKFSGDYSGTTKLTTKDVSFPVVDSEGHWG
TIC2421   STNSHTIEFPSQTIKVKPHGTTLYTGEVKQMNFSGDYSGTVKLSTKDVSFAITDSGGHWG
          :*********************:* *****::********.**.*:****.: **.***

TIC3008   DVIAAPGEKEHFLYNIEFKYSGHSIPADIRLDDASKTVVVDNSSIHFTGKLGFNMEATWKF
TIC7055   DVITAPGEKEHFLYNVFKYSGHSIPADIRLDDESKTVVVDNSSIHFTGKLGFNMEATWKF
TIC2421   DIIAAPGEEEHFLYNIEFKYSGHPIPSDIRLDDENRTVVVDNSSIHFTGKLGFNMEATWKF
          *:*:****:******: ******.**:******:.:************************

TIC3008   IPDDFQKPAVTIPHDVYMKEQASGNISKYIDQLILNKTQAK---
TIC7055   IPDDPQKPTVTIPDDVYMKEQASGNISKYIDQLIINKTQAK---
TIC2421   IPDDFKKPSVTIPNDVYLKEQASGNISKYIDQLIQTKMKSMHQ
          ****  **:****:***:****************  *  : 
```

FIG. 1

INSECT INHIBITORY PROTEINS

REFERENCE TO RELATED APPLICATION

This application claims the benefit of U.S. provisional application No. 62/206,616, filed Aug. 18, 2015, which is herein incorporated by reference in its entirety.

INCORPORATION OF SEQUENCE LISTING

The file named "MONS398US_sequence_listing.txt" containing a computer-readable form of the Sequence Listing was created on Aug. 4, 2016. This file is 66,172 bytes (measured in MS-Windows®), is contemporaneously filed by electronic submission (using the United States Patent Office EFS-Web filing system), and is incorporated into this application by reference in its entirety.

FIELD OF THE INVENTION

The invention generally relates to the field of insect inhibitory proteins. A novel class of proteins exhibiting insect inhibitory activity against agriculturally-relevant pests of crop plants and seeds are disclosed. In particular, the disclosed class of proteins is insecticidally active against agriculturally-relevant pests of crop plants and seeds, particularly Lepidopteran and Coleopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera and Coleoptera, are considered a major cause of damage to field crops, thereby decreasing crop yields over infested areas. Lepidopteran pest species which negatively impact agriculture include, but are not limited to, *Helicoverpa zea, Ostrinia nubilalis, Diatraea saccharalis, Diatraea grandiosella, Anticarsia gemmatalis, Spodoptera frugiperda, Spodoptera exigua, Agrotis ipsilon, Trichoplusia ni, Chrysodeixis includens, Heliothis virescens, Plutella xylostella, Pectinophora gossypiella, Helicoverpa armigera, Elasmopalpus lignosellus, Striacosta albicosta* and *Phyllocnistis citrella*. Coleopteran pest species which negatively impact agriculture include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly wherein the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica undecimpunctata howardii* (Southern Corn Rootworm, SCR), and a Brazilian Corn Rootworm complex (BCR) consisting of *Diabrotica viridula* and *Diabrotica speciosa*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus* and *Lysinibacillus sphaericus* ("Ls" formerly known as *Bacillus sphaericus*).

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus the inventors herein disclose a novel protein toxin family from *Bacillus thuringiensis* along with similar toxin proteins, variant proteins, and exemplary recombinant proteins that exhibit insecticidal activity against target Lepidopteran and Coleopteran pest species, particularly against Western Corn Rootworm.

SUMMARY OF THE INVENTION

Disclosed herein is a novel group of pesticidal proteins with insect inhibitory activity (toxin proteins), referred to herein as TIC2421 and TIC3008, which are shown to exhibit inhibitory activity against one or more pests of crop plants. Each of the proteins can be used alone or in combination with each other and with other insecticidal proteins and toxic agents in formulations and in planta, thus providing alternatives to insecticidal proteins and insecticide chemistries currently in use in agricultural systems.

Also disclosed herein is a novel pesticidal protein, referred herein as TIC7055, which is related to TIC2421 and TIC3008. These related proteins can be used alone or in combination with each other and with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter fragment operably linked to a polynucleotide segment encoding a pesticidal protein or fragment thereof, wherein (a) said pesticidal protein comprises the amino acid sequence selected from the group consisting of SEQ ID NO:6, SEQ ID NO:8, SEQ ID NO:10, SEQ ID NO:12, SEQ ID NO:2, SEQ ID NO:4, SEQ ID NO:20, SEQ ID NO:23, SEQ ID NO:24, SEQ ID NO:26, SEQ ID NO:28, and SEQ ID NO:30; or pesticidal fragment thereof; or (b) said pesticidal protein comprises an amino acid sequence having at least 34%, or 35%, or 40%, or 45%, or 50%, or 55%, or 60%, or 65%, or 70%, or 75%, or 80%, or 85%, or 90%, or 95%, or about 100% amino acid sequence identity to SEQ ID NO:6, SEQ ID NO:8, SEQ ID NO:10, SEQ ID NO:12, SEQ ID NO: 2, SEQ ID NO:4, SEQ ID NO:20, SEQ ID NO:23, SEQ ID NO:24, SEQ ID NO:26, SEQ ID NO:28, or SEQ ID NO:30; or (c) said polynucleotide segment hybridizes to a polynucleotide having the nucleotide sequence of SEQ ID NO:1, SEQ ID NO:3, SEQ ID NO:5, SEQ ID NO:7, SEQ ID NO:9, SEQ ID NO:11, SEQ ID NO:19, SEQ ID NO:25, SEQ ID NO:27, or SEQ ID NO:29. The recombinant nucleic acid molecule can comprise a sequence that functions to express the pesticidal protein in a plant; or the recombinant nucleic acid is expressed in a plant cell to produce a pesticidally effective amount of pesticidal protein; or the recombinant nucleic acid molecule is in operable linkage to a vector, and the vector is selected from the group consisting of a plasmid, a phagemid, a bacmid, a cosmid, and a bacterial or yeast artificial chromosome.

Another embodiment of this invention comprises host cells comprising a recombinant nucleic acid molecule of the application, wherein the host cell is selected from the group consisting of a bacterial and a plant cell. Contemplated bacterial host cells include *Agrobacterium, Rhizobium, Bacillus, Brevibacillus, Escherichia, Pseudomonas, Klebsiella, Pantoea,* and *Erwinia*; for instance wherein said *Bacillus* species is a *Bacillus cereus* or a *Bacillus thuringiensis*, said *Brevibacillus* is a *Brevibacillus laterosporus*, or said *Escherichia* is an *Escherichia coli*. Contemplated plant host cells include a dicotyledonous plant cell and a monocotyledonous plant cell. Contemplated plant cells further include an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In yet another embodiment, the pesticidal protein exhibits activity against an insect species of the order of Coleoptera, including Western Corn Rootworm, Southern Corn Rootworm, Northern Corn Rootworm, Mexican Corn Rootworm, Brazilian Corn Rootworm, or Brazilian Corn Rootworm complex consisting of *Diabrotica viridula* and *Diabrotica speciosa*.

In another embodiment, the pesticidal protein exhibits activity against an insect species of the order of Lepidoptera, including Velvet bean caterpillar, Sugarcane borer, Lesser cornstalk borer, Corn earworm, Tobacco budworm, Soybean looper, Black armyworm, Southern armyworm, Fall armyworm, Beet armyworm, Old World bollworm, Oriental leaf worm, Pink bollworm, Black cutworm, Southwestern Corn Borer, and European corn borer.

Also contemplated by the invention are plants, or parts thereof, comprising a recombinant nucleic acid molecule comprising a heterologous promoter fragment operably linked to a polynucleotide segment encoding a pesticidal protein or fragment thereof, wherein: (a) said pesticidal protein comprises the amino acid sequence selected from the group consisting of SEQ ID NO:6, SEQ ID NO:8, SEQ ID NO:10, SEQ ID NO:12, SEQ ID NO:23 and SEQ ID NO:24; or (b) said pesticidal protein comprises an amino acid sequence having at least 34%, or 35%, or 40%, or 45%, or 50%, or 55%, or 60%, or 65%, or 70%, or 75%, or 80%, or 85%, or 90%, or 95%, or about 100% amino acid sequence identity to SEQ ID NO:6, SEQ ID NO:8, SEQ ID NO:10, SEQ ID NO:12, SEQ ID NO:23, or SEQ ID NO:24; or (c) said polynucleotide segment hybridizes under stringent hybridization conditions to the complement of the nucleotide sequence as set forth in any of SEQ ID NO:5, SEQ ID NO:7, SEQ ID NO:9, SEQ ID NO:11, or SEQ ID NO:19; or (d) said plant exhibits a detectable amount of said pesticidal protein, wherein the pesticidal protein is selected from the group consisting of SEQ ID NO:6, SEQ ID NO:8, SEQ ID NO:10, SEQ ID NO:12, SEQ ID NO:23 and SEQ ID NO:24. In certain embodiments, the plant is either a dicotyledonous plant or a monocotyledonous plant. In another embodiment, the plant is further selected from the group consisting of an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising a recombinant nucleic acid molecule of the invention are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657 and a DIG-11 protein. The insect inhibitory composition may further be defined as comprising a plant cell that expresses the recombinant nucleic acid molecule.

Commodity products produced from such a plant, or part thereof, and comprising a detectable amount of the recombinant nucleic acid molecules disclosed herein are also contemplated. Such commodity products include commodity corn bagged by a grain handler, corn flakes, corn cakes, corn flour, corn meal, corn syrup, corn oil, corn silage, corn starch, corn cereal, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application.

Also contemplated herein is a method of producing seed comprising a recombinant nucleic acid molecule as disclosed in this application. The method thus comprises planting at least a first seed comprising a recombinant nucleic acid molecule disclosed herein; growing a plant from the seed; and harvesting seed from the plant, wherein the harvested seed comprises a recombinant nucleic acid molecule as disclosed herein.

In another embodiment, a plant resistant to insect infestation is contemplated, wherein the cells of said plant comprise: (a) a recombinant nucleic acid molecule encoding an insecticidally effective amount of a pesticidal protein as set forth in any of SEQ ID NO:6, SEQ ID NO:8, SEQ ID NO:10, SEQ ID NO:12, SEQ ID NO:23, or SEQ ID NO:24; or (b) an insecticidally effective amount of a protein comprising an amino acid sequence having at least 34%, or 35%, or 40%, or 45%, or 50%, or 55%, or 60%, or 65%, or 70%, or 75%, or 80%, or 85%, or 90%, or 95%, or about 100% amino acid sequence identity to SEQ ID NO:6, SEQ ID NO:8, SEQ ID NO:10, SEQ ID NO:12, SEQ ID NO:23, or SEQ ID NO:24.

Also disclosed herein are methods for controlling a Coleopteran or Lepidopteran species pest, and controlling a Coleopteran or Lepidopteran species pest infestation of a plant, particularly a crop plant. The method comprises contacting the pest with an insecticidally effective amount of one or more pesticidal proteins as set forth in any of SEQ ID NO:6, SEQ ID NO:8, SEQ ID NO:10, SEQ ID NO:12, SEQ ID NO:23, or SEQ ID NO:24; or contacting the pest with an insecticidally effective amount of one or more pesticidal proteins comprising an amino acid sequence having at least 34%, or 35%, or 40%, or 45%, or 50%, or 55%, or 60%, or 65%, or 70%, or 75%, or 80%, or 85%, or 90%, or 95%, or about 100% amino acid sequence identity to SEQ ID NO:6, SEQ ID NO:8, SEQ ID NO:10, SEQ ID NO:12, SEQ ID NO:23, or SEQ ID NO:24.

Further contemplated are methods of detecting the presence of a recombinant nucleic acid molecule as disclosed herein, in a sample comprising plant genomic DNA, comprising: (a) contacting the sample with a nucleic acid probe that hybridizes under stringent hybridization conditions with genomic DNA from a plant comprising a DNA molecule of claim 1, and does not hybridize under such hybridization conditions with genomic DNA from an otherwise isogenic plant that does not comprise the recombinant nucleic acid molecule as disclosed, wherein: the probe is homologous or complementary to all or part of SEQ ID NO:1, SEQ ID NO:3, SEQ ID NO:5, SEQ ID NO:7, SEQ ID NO:9, SEQ ID NO:11, or SEQ ID NO:19; or to a sequence that encodes a pesticidal protein comprising an amino acid sequence having at least 65%, or 70%, or 75%, or 80%, or 85%, or 90%, or 95%, or 98%, or 99%, or about 100% amino acid sequence identity to SEQ ID NO:6, SEQ ID NO:8, SEQ ID NO:10, SEQ ID NO:12, SEQ ID NO:2, SEQ ID NO:4, SEQ ID NO:20, SEQ ID NO:23, SEQ ID NO:24, SEQ ID NO:26, SEQ ID NO:28, and SEQ ID NO:30; or a pesticidal fragment thereof; (b) subjecting the sample and probe to stringent hybridization conditions; and (c) detecting hybridization of the probe with DNA of the sample.

Also contemplated are methods of detecting the presence of a pesticidal protein or fragment thereof in a sample comprising protein, wherein said pesticidal protein comprises the amino acid sequence of SEQ ID NO:6, SEQ ID NO:8, SEQ ID NO:10, SEQ ID NO:12, SEQ ID NO:2, SEQ ID NO:4, SEQ ID NO:20, SEQ ID NO:23, SEQ ID NO:24, SEQ ID NO:26, SEQ ID NO:28, or SEQ ID NO:30; or a pesticidal fragment thereof; or said pesticidal protein comprises an amino acid sequence having at least 65%, or 70%, or 75%, or 80%, or 85%, or 90%, or 95%, or 98%, or 99% or about 100% amino acid sequence identity to SEQ ID NO:6, SEQ ID NO:8, SEQ ID NO:10, SEQ ID NO:12, SEQ ID NO:2, SEQ ID NO:4, SEQ ID NO:20, SEQ ID NO:23, SEQ ID NO:24, SEQ ID NO:26, SEQ ID NO:28, or SEQ ID NO:30; or a pesticidal fragment thereof; comprising: (a) contacting the sample with an immunoreactive antibody; and (b) detecting the presence of the protein. In certain embodiments of the methods, the step of detecting comprises an ELISA, or a western blot.

BRIEF DESCRIPTION OF THE DRAWINGS

FIG. 1 illustrates the alignment of the pesticidal proteins TIC2421 (SEQ ID NO:2), TIC3008 (SEQ ID NO:4), and TIC7055 (SEQ ID NO:20) wherein "*" indicates identical amino acids and "." and ":" indicate conserved amino acids in the alignment and "-" in the protein sequences indicates gaps.

BRIEF DESCRIPTION OF THE SEQUENCES

Figure 2:
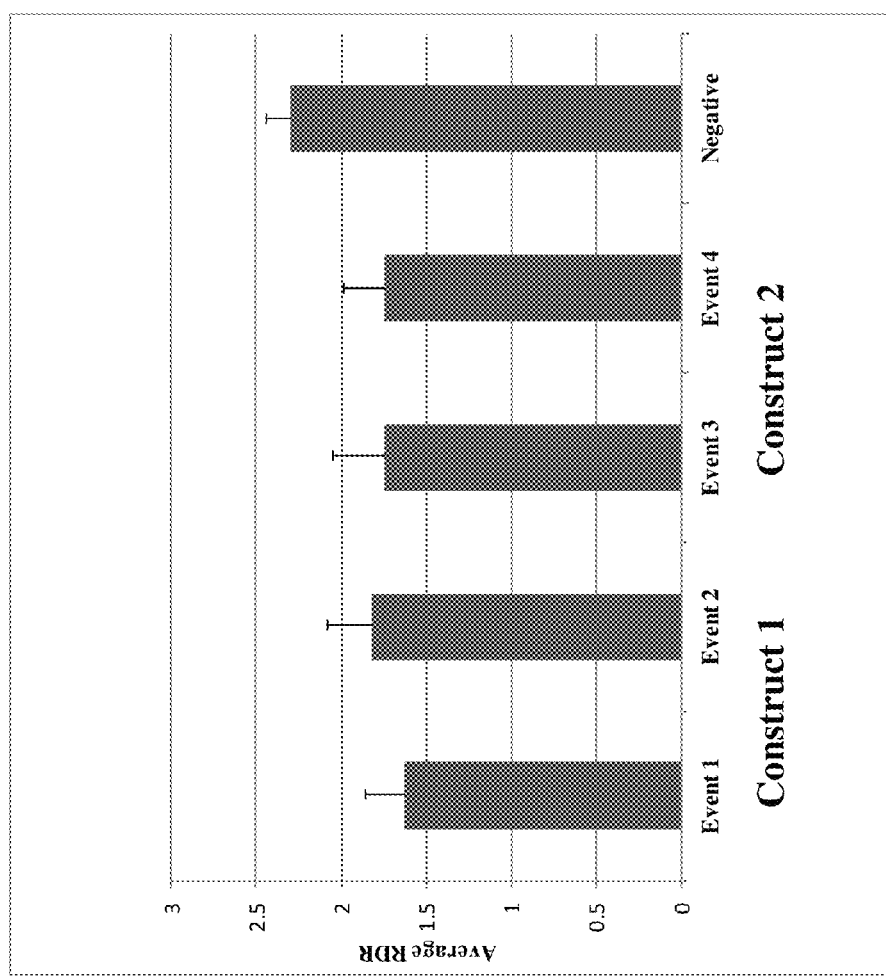
FIG. 2 illustrates average root damage rating ("RDR") seen from four independent events each comprising one of two constructs, as compared to a negative control.

SEQ ID NO:1 is a recombinant nucleic acid sequence obtained from a *Bacillus thuringiensis* species encoding a TIC2421 pesticidal protein from an open reading frame at nucleotide position 1-1188 and a translation termination codon.

SEQ ID NO:2 is the amino acid sequence translation of the TIC2421 precursor protein from the open reading frame as set forth in SEQ ID NO:1.

SEQ ID NO:3 is a recombinant nucleic acid sequence obtained from a *Bacillus thuringiensis* species encoding a TIC3008 pesticidal protein from an open reading frame at nucleotide position 1-1200 and a translation termination codon.

SEQ ID NO:4 is the amino acid sequence translation of the TIC3008 precursor protein from the open reading frame as set forth in SEQ ID NO:3.

SEQ ID NO:5 is a synthetic coding sequence encoding a mature TIC2421 (mTIC2421) pesticidal protein.

SEQ ID NO:6 is the amino acid sequence translation of the mature TIC2421 (mTIC2421) pesticidal protein from the open reading frame as set forth in SEQ ID NO:5.

SEQ ID NO:7 is a synthetic coding sequence encoding a mature TIC3008 (mTIC3008) pesticidal protein.

SEQ ID NO:8 is the amino acid sequence translation of the mature TIC3008 (mTIC3008) pesticidal protein from the open reading frame as set forth in SEQ ID NO:7.

SEQ ID NO:9 is a synthetic coding sequence encoding a plastid targeted mature TIC2421 (CTP/mTIC2421) pesticidal protein.

SEQ ID NO:10 is the amino acid sequence translation of the plastid targeted mature TIC2421 (CTP/mTIC2421) pesticidal protein from the open reading frame as set forth in SEQ ID NO:9.

SEQ ID NO:11 is a synthetic coding sequence encoding a plastid targeted mature TIC3008 CTP/mTIC3008) pesticidal protein.

SEQ ID NO:12 is the amino acid sequence translation of the plastid targeted mature TIC3008 (CTP/mTIC3008) pesticidal protein from the open reading frame as set forth in SEQ ID NO:11.

SEQ ID NO:13 is a nucleic acid sequence encoding the membrane transiting segment corresponding to the N-terminal first 37 amino acids of TIC2421 which is encoded by nucleotides 1-111 of SEQ ID NO:1.

SEQ ID NO:14 is the amino acid sequence translation of the nucleic acid sequence encoding the membrane transiting segment of TIC2421 as set forth in SEQ ID NO:13.

SEQ ID NO:15 is a nucleic acid sequence encoding the membrane transiting segment corresponding to the N-terminal first 37 amino acids of TIC3008 which is encoded by nucleotides 1-111 of SEQ ID NO:3.

SEQ ID NO:16 is the amino acid sequence translation of the nucleic acid sequence encoding the membrane transiting segment of TIC3008 as set forth in SEQ ID NO:15.

SEQ ID NO:17 is a nucleic acid sequence encoding a chloroplast targeting signal peptide which is operably linked and in phase to both the synthetic mature coding sequences of TIC2421 (mTIC2421) set forth in SEQ ID NO:5 and TIC3008 (mTIC3008) as set forth in SEQ ID NO:7.

SEQ ID NO:18 is the amino acid translation of the nucleic acid sequence encoding the chloroplast targeting signal peptide as set forth in SEQ ID NO:17.

SEQ ID NO:19 is a recombinant nucleic acid sequence obtained from a *Bacillus thuringiensis* species encoding a TIC7055 pesticidal protein from an open reading frame at nucleotide position 1-1200 and a translation termination codon.

SEQ ID NO:20 is the amino acid sequence translation of the TIC7055 precursor protein from the open reading frame as set forth in SEQ ID NO:19.

SEQ ID NO:21 is a nucleic acid sequence encoding the membrane transiting segment corresponding to the N-terminal first 37 amino acids of TIC7055 which is encoded by nucleotides 1-111 of SEQ ID NO:19.

SEQ ID NO:22 is the amino acid sequence translation of the nucleic acid sequence encoding the membrane transiting segment of TIC7055 as set forth in SEQ ID NO:21.

SEQ ID NO:23 is the amino acid sequence of the mature TIC7055 (mTIC7055) pesticidal protein which is encoded by a synthetic DNA sequence used for expression in plants.

SEQ ID NO:24 is the amino acid sequence of a plastid targeted TIC7055 (CTP/mTIC7055) which is encoded by a synthetic DNA sequence used for expression in plants.

SEQ ID NO:25 is a recombinant nucleic acid sequence obtained from a *Bacillus thuringiensis* species encoding a TIC2421 pesticidal protein with a Histidine tag operably linked to the 3' end, herein referred to as TIC2421_His.

SEQ ID NO:26 is the amino acid sequence of TIC2421_His encoded by SEQ ID NO:25.

SEQ ID NO:27 is a recombinant nucleic acid sequence obtained from a *Bacillus thuringiensis* species encoding a TIC3008 pesticidal protein with a Histidine tag operably linked to the 3' end, herein referred to as TIC3008_His.

SEQ ID NO:28 is the amino acid sequence of TIC3008_His encoded by SEQ ID NO:27.

SEQ ID NO:29 is a recombinant nucleic acid sequence obtained from a *Bacillus thuringiensis* species encoding a TIC7055 pesticidal protein with a Histidine tag operably linked to the 3' end, herein referred to as TIC7055_His.

SEQ ID NO:30 is the amino acid sequence of TIC7055_His encoded by SEQ ID NO:29.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel pesticidal proteins exemplified by TIC2421 and TIC3008 are disclosed herein, and address each of these needs, particularly against a broad spectrum of Coleopteran and Lepidopteran insect pests, and more particularly against corn rootworm pest species. Another novel insecticidal protein is exemplified by TIC7055 which is related to TIC2421 and TIC3008 and is also disclosed.

Reference in this application to "TIC2421", "TIC2421 protein", "TIC2421 protein toxin", "TIC2421 toxin protein", "TIC2421 pesticidal protein", "TIC2421-related toxins", "TIC2421-related toxin proteins", "TIC3008", "TIC3008 protein", "TIC3008 protein toxin", "TIC3008 toxin protein", "TIC3008 pesticidal protein", "TIC3008-related toxins", or "TIC3008-related toxin proteins", "TIC7055", "TIC7055 protein", "TIC7055 protein toxin", "TIC7055 toxin protein", "TIC7055 pesticidal protein", "TIC7055-related toxins", or "TIC7055-related toxin proteins", and the like, refer to any novel pesticidal protein or insect inhibitory protein, that comprises, that consists of, that is substantially homologous to, that is similar to, or that is derived from any pesticidal protein or insect inhibitory protein sequence of TIC2421 (SEQ ID NO:2), TIC3008 (SEQ ID NO:4), or TIC7055 (SEQ ID NO:20) and pesticidal or insect inhibitory segments thereof, or combinations thereof, that confer activity against Coleopteran pests and Lepidopteran pests, including any protein exhibiting pesticidal or insect inhibitory activity if alignment of such protein with TIC2421, TIC3008, or TIC7055 results in amino acid sequence identity of any fraction percentage form about 34% to about 100% percent. The TIC2421, TIC3008, and TIC7055 proteins include the precursor forms as well as the mature length forms (both plastid-targeted and non-plastid targeted) of the proteins.

The term "segment" or "fragment" is used in this application to describe consecutive amino acid or nucleic acid sequences that are shorter than the complete amino acid or nucleic acid sequence describing a TIC2421, TIC3008, or TIC7055 protein. A segment or fragment exhibiting insect inhibitory activity is also disclosed in this application if alignment of such segment or fragment, with the corresponding section of the TIC2421 protein set forth in SEQ ID NO:2, or TIC3008 protein set forth in SEQ ID NO:4, or TIC7055 protein set forth in SEQ ID NO:20 results in amino acid sequence identity of any fraction percentage from about 34 to about 100 percent between the segment or fragment and the corresponding section of the TIC2421, TIC3008, or TIC7055 protein.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC2421, TIC3008, or TIC7055 protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, and/or fecundity of an insect pest; or any measurable decrease in the adverse effects caused by any particular target pest (including but not limited to insects of the order Lepidoptera or Coleoptera) feeding on a plant, such activity caused by this protein, protein fragment, protein segment or polynucleotide. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents may include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopteran and Coleopteran, as well as protein toxins that are used to control other plant pests such as Cry and Cyt proteins available in the art for use in controlling Hemipteran and Homopteran species.

It is intended that reference to a pest, particularly a pest of a crop plant, means insect pests of crop plants, particularly those that are controlled by the TIC2421, TIC3008, or TIC7055 protein toxin class. However, reference to a pest can also include Hemipteran and Homopteran insect pests of plants, as well as nematodes and fungi when toxic agents targeting these pests are co-localized or present together with the TIC2421 protein, and/or TIC3008 protein, and/or TIC7055, or a protein that is 34 to about 100 percent identical to TIC2421, TIC3008, or TIC7055.

The TIC2421, TIC3008, and TIC7055 proteins are related by common function and exhibit insecticidal activity towards insect pests from the Coleoptera and Lepidoptera insect species, including adults, pupae, larvae, and neonates. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), Southern armyworm (*Spodoptera eridania*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), surgarcane borer (*Diatraea* saccharalis), spiny bollworm (*Earias insulana*), spotted bollworm (*Earias vittella*), American bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), diamondback moth (*Plutella xylostella*), beet armyworm (*Spodoptera exigua*), tobacco cutworm (*Spodoptera litura*, also known as cluster caterpillar), and tomato leafminer (*Tuta absoluta*).

The insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly when the pest is Western Corn Rootworm (*Diabrotica virgifera virgifera*, WCR), Northern Corn Rootworm (*Diabrotica barberi*, NCR), Mexican Corn Rootworm (*Diabrotica virgifera zeae*, MCR), Brazilian Corn Rootworm (*Diabrotica balteata*, BZR), Southern Corn Rootworm (*Diabrotica undecimpunctata howardii*, SCR) and a Brazilian Corn Rootworm complex (BCR, consisting of *Diabrotica viridula* and *Diabrotica speciosa*). The insects of Hemiptera include but are not limited to, Western tarnished plant bug (*Lygus hesperus*), Tarnished plant bug (*Lygus lineolaris*), and Cotton fleahopper (*Pseudatomoscelis seriatus*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding a insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in this application, an open reading frame (ORF) encoding TIC2421 (SEQ ID NO:1) was discovered in DNA obtained from *Bacillus thuringiensis* strain CFB199510. An ORF (SEQ ID NO:3) encoding TIC3008 was discovered in DNA obtained from *Bacillus thuringiensis* strain CFB005050. Finally, an ORF (SEQ ID NO:19) encoding TIC7055 was discovered in DNA obtained from *Bacillus thuringiensis* strain CFB262371. The respective coding sequences were cloned and expressed in microbial host cells to produce recombinant proteins used in bioassays. Cytosolic and chloroplast targeted mature forms of TIC2421, TIC3008 and TIC7055 encoded by synthetic DNA sequences used for optimal expression in plants were expressed in transgenic corn plants. The leaf tissues derived from these transgenic corn plants can be used in bioassay. Bioassay using microbial host cell-derived proteins of TIC2421 demonstrated activity against the Coleopteran pests Colorado potato beetle (*Leptinotarsa decemlineata*, CPB) and Western Corn Rootworm (*Diabrotica virgifera virgifera*, WCR). Microbial host cell-derived proteins of TIC3008 demonstrated activity against the Coleopteran pests Colorado potato beetle (*Leptinotarsa decemlineata*, CPB) and Western Corn Rootworm (*Diabrotica virgifera virgifera*, WCR), and Northern Corn Rootworm (*Diabrotica barberi*, NCR). Microbial host cell-derived proteins of TIC7055 demonstrated activity against the Coleopteran Colorado potato beetle (*Leptinotarsa decemlineata*, CPB) and the Hemipteran pest Tarnished Plant Bug (*Lygus lineolaris*, TPB). Leaf samples of transgenic corn plants transformed with mature forms of TIC2421 protein and TIC3008 protein demonstrated activity against Lepidopteran insect pests. The mature TIC2421 (mTIC2421) expressed in corn demonstrated activity against the Lepidopteran species Fall armyworm (*Spodoptera frugiperda*, FAW) and Southwestern Corn Borer (*Diatraea grandiosella*, SWCB). The mature TIC3008 protein (mTIC3008) expressed in transgenic corn demonstrated activity against the Lepidopteran species Corn earworm (*Helicoverpa zea*, CEW), and Fall armyworm (*Spodoptera frugiperda*, FAW).

A surprising feature of the TIC2421, TIC3008, and TIC7055 proteins is the presence of a signal peptide, a N-terminal amino acid segment corresponding to amino acid position 1 to 37 for TIC2421 TIC3008, and TIC7055. It is believed that the presence of a signal peptide is found in proteins that are self-transported across a membrane and, in the process of transiting the membrane, the signal peptide can be cleaved off. Each of these N-terminal amino acid segments may be omitted from the respective protein and the polynucleotide sequence encoding the respective amino acid segment may also be omitted. Protein toxin segments lacking the N-terminal amino acid segment signal peptide are referred to in this application as "mature TIC2421, TIC3008, and TIC7055 toxin proteins". The mature TIC2421, TIC3008, TIC7055 toxin proteins lack amino acids 2 to 37 relative to the native bacterial protein amino acid sequence, but retain an initiating methionine at position one in the protein sequence and an "ATG" at the beginning of the synthetic coding sequence to allow for proper translation to occur in the host plant cell. In general, the mature versions of the TIC2421, TIC3008, and TIC7055 proteins are annotated in this application with the letter "m" preceding the name of the toxin to differentiate the mature sequence from the full length native sequence. For example, the mature version of the amino acid sequence for TIC2421 (SEQ ID NO:2) is mTIC2421 (SEQ ID NO:6). The mature version of the amino acid sequence for TIC3008 (SEQ ID NO:4) is mTIC3008 (SEQ ID NO:8). The mature version of the amino acid sequence for TIC7055 (SEQ ID NO:20) is mTIC7055 (SEQ ID NO:23).

For expression in plant cells, the TIC2421, TIC3008, and TIC7055 proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the mature TIC2421, TIC3008 or TIC7055 toxin protein to the chloroplast, a sequence encoding a chloroplast transit peptide is placed 5' in operable linkage and in frame to a synthetic coding sequence encoding the mature TIC2421, TIC3008 or TIC7055 toxin protein that has been designed for optimal expression in plant cells.

Additional toxin protein sequences related to TIC2421, TIC3008 and TIC7055 can be created by using the naturally occurring amino acid sequences of TIC2421, TIC3008 and TIC7055 to create novel proteins with novel properties. The TIC2421, TIC3008 and TIC7055 toxin proteins can be aligned to combine differences at the amino acid sequence level into novel amino acid sequence variants and making appropriate changes to the recombinant nucleic acid sequence encoding the variants.

Fragments of TIC2421, TIC3008, TIC7055 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC2421, TIC3008, TIC7055 or derived protein variants, but should retain the insect inhibitory activity of at least TIC2421, TIC3008, or TIC7055. Truncated N-terminal or C-terminal deletion variants include, but are not limited to, TIC2421 protein, TIC3008 protein, or TIC7055 protein, or protein variants thereof, that lack amino acid residues from either the N-terminus or the C-terminus. For example, N-terminal amino acid residues 2 to 37 of TIC2421 protein can be deleted resulting in a toxin protein having the amino acid sequence of 1 and 38-396 of SEQ ID NO:2.

Proteins that resemble the TIC2421, TIC3008, and TIC7055 proteins can be identified and compared to each other using various computer based algorithms known in the art (see Tables 1 and 2). Amino acid sequence identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran or Coleopteran insect species is related to TIC2421, TIC3008, or TIC7055 if the protein is used in a query, e.g., in a Clustal W alignment, and the proteins of the present invention as set forth as mTIC2421, mTIC3008, and mTIC7055 are identified as hits in such alignment in which the query protein exhibits at least 34% to about 100% amino acid identity along the length of the query protein that is about 34%, 35%, 40%, 50%, 60%, 70%, 75%, 76%, 77%, 78%, 79%, 80%, 81%, 82%, 83%, 84%, 85%, 85%, 87%, 88%, 89%, 90%, 91%, 92%, 93%, 94%, 95%, 96%, 97%, 98%, 99%, 100%, or any fraction percentage in this range, as compared with the subject protein.

Exemplary proteins TIC2421, TIC3008, and TIC7055 were aligned with each other using a Clustal W algorithm. A pair-wise matrix of percent amino acid sequence identities for each of the full-length proteins was created, as reported in Table 1. A pair-wise matrix of percent amino acid sequence identities for each of the mature proteins was created, as reported in Table 2.

TABLE 1

Pair-wise matrix display of exemplary full-length proteins.

| Protein (SEQ ID NO:) | TIC2421 (SEQ ID NO: 2) | TIC3008 (SEQ ID NO: 4) | TIC7055 (SEQ ID NO: 20) |
|---|---|---|---|
| TIC2421 (SEQ ID NO: 2) | — | 75 (297) | 74.2 (294) |
| TIC3008 (SEQ ID NO: 4) | 74.3 (297) | — | 94 (376) |
| TIC7055 (SEQ ID NO: 20) | 73.5 (294) | 94 (376) | — |

Table Description:
Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

TABLE 2

Pair-wise matrix display of exemplary mature proteins.

| Protein (SEQ ID NO:) | mTIC2421 (SEQ ID NO: 6) | mTIC3008 (SEQ ID NO: 8) | mTIC7055 (SEQ ID NO: 23) |
|---|---|---|---|
| mTIC2421 (SEQ ID NO: 6) | — | 75.8 (273) | 74.7 (269) |
| mTIC3008 (SEQ ID NO: 8) | 75 (273) | — | 94.5 (344) |
| mTIC7055 (SEQ ID NO: 23) | 73.9 (269) | 94.5 (344) | — |

Table Description:
Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

The full-length and mature TIC2421, TIC3008 and TIC7055 proteins can also be related by primary structure (conserved amino acid motifs), by length (about 396 for the full-length proteins and about 360 amino acids for the mature proteins) and by other characteristics. Certain characteristics of the full-length and mature forms of TIC2421, TIC3008 and TIC7055 protein toxins are reported in Tables 3 and 4.

TABLE 3

Selected characteristics of the full-length TIC2421, TIC3008, and TIC7055 proteins.

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| TIC2421 | 44009.94 | 396 | 7.0106 | 3.5 | 52 | 42 | 180 | 216 |
| TIC3008 | 44334.52 | 400 | 7.0165 | 3.5 | 54 | 44 | 182 | 218 |
| TIC7055 | 44374.49 | 400 | 6.0933 | −3.0 | 52 | 49 | 182 | 218 |

TABLE 4

Selected characteristics of the mature mTIC2421, mTIC3008, and TIC7055 proteins.

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| mTIC2421 | 40115.2 | 360 | 6.1881 | −2.5 | 46 | 42 | 156 | 204 |
| mTIC3008 | 40398.76 | 364 | 6.1892 | −2.5 | 47 | 43 | 161 | 203 |
| mTIC7055 | 40537.91 | 364 | 5.3906 | −7.0 | 47 | 48 | 160 | 204 |

As described further in the Examples of this application, recombinant nucleic acid molecule sequences encoding mTIC2421 and mTIC3008 were designed for use in plants. Exemplary recombinant nucleic acid molecule sequences that were designed for use in plants encoding the mature form of the insect inhibitory mTIC2421, mTIC3008, plastid-targeted mTIC2421 and plastid-targeted mTIC3008 proteins are set forth in SEQ ID NO:5, SEQ ID NO:7, SEQ ID NO:9, and SEQ ID NO:11.

Expression cassettes and vectors containing these synthetic nucleic acid molecule sequences are constructed and introduced into corn plant cells in accordance with transformation methods and techniques known in the art. Transformed cells are regenerated into transformed plants that are observed to be expressing insect inhibitory TIC2421, TIC3008, or TIC7055 mature form proteins (mTIC2421, mTIC3008, and mTIC7055). Plants can be derived from the plant cells by regeneration, seed, pollen, or meristem transformation techniques. Methods for transforming plants are known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) *Transgenic Res.* 7:213-222 (sugarcane) all of which are incorporated herein by reference in their entirety.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. As understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Expression cassettes and vectors containing recombinant nucleic acid molecule sequences for expression of mTIC2421 and mTIC3008 were constructed and introduced into corn plant cells. Transformed cells were regenerated into transformed plants that were observed to be expressing mTIC2421, mTIC3008, plastid-targeted mTIC2421 and plastid-targeted mTIC3008 proteins. To test pesticidal activity, bioassays were performed in the presence of Lepidopteran pest larvae using plant leaf disks obtained from the transformed plants.

The insect inhibitory activity of exemplary TIC2421, TIC3008, mTIC2421 and mTIC3008 are related in common function and exhibit insecticidal activity towards Coleoptera and Lepidoptera insect species, including adults, pupae, larvae and neonates.

Recombinant nucleic acid molecule compositions that encode TIC2421, TIC3008, TIC7055, mTIC2421, mTIC3008, and mTIC7055 are contemplated. For example, mTIC2421, mTIC3008 and mTIC7055 proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the mTIC2421, or mTIC3008, or mTIC7055 protein encoding sequences for expression of the protein in plants or a Bt-functional promoter operably linked to a TIC2421, or TIC3008, or TIC7055 protein encoding sequence for expression of the protein in a Bt bacterium or other *Bacillus* species. Other elements can be operably linked to the mTIC2421, or mTIC3008, or mTIC7055 protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:7, SEQ ID NO:9, SEQ ID NO:11, and SEQ ID NO:19 that encodes the respective polypeptides or proteins having the amino acid sequence as set forth in SEQ ID NO:2, SEQ ID NO:4, SEQ ID NO:6, SEQ ID NO:8, SEQ ID NO:10, SEQ ID NO:12, and SEQ ID NO:20. A heterologous promoter can also be operably linked to synthetic DNA coding sequences encoding a plastid targeted mTIC7055 (CTP/mTIC7055, presented as SEQ ID NO:24) and untargeted mTIC7055 (presented as SEQ ID NO:23). The codons of a recombinant nucleic acid molecule encoding for proteins disclosed herein can be substituted by synonymous codons (known in the art as a silent substitution).

A recombinant DNA construct comprising a TIC2421, TIC3008, TIC7055, mTIC2421, mTIC3008, or mTIC7055 protein encoding sequence can further comprise a region of DNA that encodes for one or more insect inhibitory agents which can be configured to concomitantly express or co-express with a DNA sequence encoding a TIC2421, TIC3008, TIC7055, mTIC2421, mTIC3008, mTIC7055 protein, a protein different from a TIC2421, TIC3008, TIC7055, mTIC2421, mTIC3008, or mTIC7055 protein, an insect inhibitory dsRNA molecule, or an ancillary protein.

Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of TIC2421, TIC3008, TIC7055, mTIC2421, mTIC3008, or mTIC7055 are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes each expressing a different protein or other agent such as one or more dsRNA molecules.

Recombinant nucleic acid molecules or recombinant DNA constructs comprising a TIC2421, TIC3008, TIC7055, mTIC2421, mTIC3008, or an mTIC7055 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC2421, TIC3008, TIC7055, mTIC2421, mTIC3008, or mTIC7055 protein encoding sequence in a host cell, or subsequent expression of the encoded polypeptide. An exogenous recombinant polynucleotide or recombinant DNA construct that comprises a TIC2421, TIC3008, TIC7055, mTIC2421, mTIC3008, or TIC7055 protein encoding sequence and that is introduced into a host cell is referred in this application as a "transgene".

Transgenic bacteria, transgenic plant cells, transgenic plants, and transgenic plant parts that contain a recombinant polynucleotide that expresses any one or more of the TIC2421, TIC3008, TIC7055, mTIC2421, mTIC3008, or mTIC7055 protein encoding sequences are provided in this application. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous or monocotyledonous plant. The term "plant cell" or "plant" can also include but is not limited to an alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect-inhibitory, such as Coleoptera- or Lepidoptera-inhibitory amounts of a TIC2421, TIC3008, TIC7055, mTIC2421, mTIC3008, or mTIC7055 protein are provided. Such plants can be made by introducing a recombinant polynucleotide that encodes any of the proteins provided in this application into a plant cell, and selecting a plant derived from said plant cell that expresses an insect, Coleoptera-, or Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC2421, TIC3008, TIC7055, mTIC2421, mTIC3008, mTIC7055 protein, or a detectable amount of a nucleic acid sequence encoding part or all of such a protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC2421, TIC3008, TIC7055, mTIC2421, mTIC3008, or mTIC7055 protein.

Plants expressing the TIC2421, TIC3008, TIC7055, mTIC2421, mTIC3008, or mTIC7055 proteins can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

TIC2421, TIC3008, and TIC7055 protein-encoding sequences and sequences having a substantial percentage identity to TIC2421, TIC3008, and TIC7055 can be identified using methods known to those of ordinary skill in the art such as polymerase chain reaction (PCR), thermal amplification and hybridization. For example, the proteins TIC2421, TIC3008, and TIC7055 can be used to produce antibodies that bind specifically to related proteins, and can be used to screen for and to find other protein members that are closely related.

Furthermore, nucleotide sequences encoding the TIC2421, TIC3008, and TIC7055 toxin proteins, or a portion thereof, can be used as probes and primers for screening to identify other members of the class using thermal-cycle or isothermal amplification and hybridization methods. For example, oligonucleotides derived from sequences as set forth in any of SEQ ID NO:5 and SEQ ID NO:7 can be used to determine the presence or absence of a TIC2421, TIC3008, TIC7055, mTIC2421, mTIC3008, and mTIC7055 transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:5 and SEQ ID NO:7, or an analogous sequence for TIC7055, can be used to detect a TIC2421, TIC3008 or TIC7055 transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NO:5 and SEQ ID NO:7. Such "mutagenesis" oligonucleotides are useful for identification of TIC2421, TIC3008 or TIC7055 amino acid sequence variants exhibiting a range of insect inhibitory activity or varied expression in transgenic plant host cells.

Likewise, oligonucleotides derived from synthetic sequences encoding an mTIC7055 can be used to determine the presence or absence of an mTIC7055 transgene in a deoxyribonucleic acid sample derived from a commodity product, derived from pooled sources where only a fraction of the commodity product is derived from a transgenic plant containing the mTIC7005 encoding synthetic sequence. Such oligonucleotides can also be used to introduce nucleotide sequence variation in the mTIC7005 encoding sequence and such oligonucleotides can be useful in identifying TIC7055 amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be, for instance, any of the nucleotide sequences presented as SEQ ID NO:1, or SEQ ID NO:3, or SEQ ID NO:19 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC2421, or TIC3008, or TIC7055. This application contemplates the use of these, and other identification methods known to those of ordinary skill in the art, to identify TIC2421, or TIC3008, or TIC7055 protein-encoding sequences and sequences having a substantial percentage identity to TIC2421, or TIC3008, or TIC7055 protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC2421, TIC3008, or TIC7055 proteins to derive additional useful embodiments including assembly of segments of TIC2421, TIC3008, or TIC7055 proteins with segments of diverse proteins different from TIC2421, TIC3008, or TIC7055 and related proteins. The TIC2421, TIC3008, or TIC7055 proteins may be subjected to alignment to each other and to other *Bacillus* pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

This disclosure further contemplates the engineering of improved variants of TIC2421, TIC3008, and TIC7055 toxin protein in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

Methods of controlling insects, in particular Lepidoptera or Coleoptera infestations of crop plants, with the TIC2421, TIC3008, and TIC7055 proteins are also disclosed in this application. Such methods can comprise growing a plant comprising an insect-, Coleoptera- or Lepidoptera-inhibitory amount of a TIC2421, TIC3008, or TIC7055 toxin protein. In certain embodiments, such methods can further comprise any one or more of: (i) applying any composition comprising or encoding a TIC2421, TIC3008, or TIC7055 toxin protein to a plant or a seed that gives rise to a plant; and (ii) transforming a plant or a plant cell that gives rise to a plant with a polynucleotide encoding a TIC2421, TIC3008, or TIC7055 toxin protein. In general, it is contemplated that a TIC2421, TIC3008, or TIC7055 toxin protein can be provided in a composition, provided in a microorganism, or provided in a transgenic plant to confer insect inhibitory activity against Lepidopteran or Coleopteran insects.

In certain embodiments, a recombinant nucleic acid molecule of TIC2421, TIC3008, or TIC7055 toxin proteins is the insecticidally active ingredient of an insect inhibitory composition prepared by culturing recombinant *Bacillus* or any other recombinant bacterial cell transformed to express a TIC2421, TIC3008, or TIC7055 toxin protein under conditions suitable to express the TIC2421, TIC3008, or TIC7055 toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC2421, TIC3008, or TIC7055 can further comprise at least one additional polypeptide that exhibits insect inhibitory activity against the same Lepidopteran or Coleopteran insect species, but which is different from the TIC2421, TIC3008, or TIC7055 toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, axmi209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594(A2)), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), Axmi205 (U.S. Patent Publication 2014-0298538 A1), axmi207 (U.S. Patent Publication 2013-0303440 A1), AXMI218, AXMI220 (U.S. Patent Publication 20140245491A1), Axmi221z, axmi223z (U.S. Patent Publication 2014-0196175 A1), AXMI279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914). IP3 and variants thereof (U.S. Patent Publication 2012-0210462 A1), and $\overline{\omega}$-Hexatoxin-Hv1a (U.S. Patent Application Publication US2014-0366227 A1).

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran or Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC2421, or TIC3008, or TIC7055 pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery, Cloning, and Expression of TIC2421 and TIC3008

Sequences encoding three different but novel *Bacillus thuringiensis* (Bt) pesticidal proteins were identified, cloned, sequence confirmed and tested in insect bioassay. The pesticidal proteins, TIC2421 isolated from Bt strain CFB199510, TIC3008 isolated from Bt strain CFB005050, and TIC7055 isolated from Bt strain CFB262371 belong to the ETX_MTX2 protein family (pfam). TIC2421 is approximately 74% identical to TIC3008 and TIC7055. TIC3008 and TIC7055 are approximately 94% identical to each other. FIG. 1 shows a global, Clustal W alignment of the two pesticidal proteins along with TIC7055 (described in Example 5) wherein "*" indicates identical amino acids and "." and ":" indicate conserved amino acids in the alignment and "−" in the protein sequences indicates gaps.

Polymerase chain reaction (PCR) primers were designed to amplify a full length copy of the coding regions for TIC2421, TIC3008, and TIC7055 from total genomic DNA isolated from each of the respective Bt strains. The PCR amplicons also included the translational initiation and termination codons of each coding sequence. Examination of the predicted amino acid sequence of each protein sequence using the signal peptide computer algorithm SignalP (Petersen, et. al (2011), *Nature Methods*, 8:785-786) predicted the presence of a membrane transiting segment corresponding to the N-terminal first 37 amino acids. The predicted membrane transiting segment, or signal peptide, of TIC2421 is presented as SEQ ID NO:14 and is encoded by SEQ ID NO:13. The predicted membrane transiting segment, or signal peptide, of TIC3008 is presented as SEQ ID NO:16 and encoded by SEQ ID NO:15. The predicted membrane transiting segment, or signal peptide, of TIC7055 is presented as SEQ ID NO:22 and encoded by SEQ ID NO:21.

Each of the amplicons were cloned using methods known in the art into two different Bt expression vectors in operable linkage with a Bt expressible promoter. One Bt expression vector comprised a promoter that is on during sporulation of the *bacillus*. The other expression vector comprised a non-sporulation promoter. In addition, each of the amplicons were cloned into a vector used for protein expression in *Escherichia coli* (*E. coli*). For isolation of the *E. coli* expressed proteins, a Histidine tag was operably linked to the expressed coding sequences for facilitate column purification of the protein.

The coding sequences and their respective protein sequences used for bacterial expression are presented in Table 5 below.

TABLE 5

Toxin coding sequences and corresponding protein sequences used for expression in Bt and *E. coli*.

| Toxin | DNA Coding Sequence SEQ ID NO: | Protein SEQ ID NO: | Bacterial Expression Host |
|---|---|---|---|
| TIC2421 | 1 | 2 | Bt |
| TIC3008 | 3 | 4 | Bt |

TABLE 5-continued

Toxin coding sequences and corresponding protein sequences used for expression in Bt and *E. coli*.

| Toxin | DNA Coding Sequence SEQ terium-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple transformation events from each binary vector were assessed against Corn earworm (CEW, *Helicoverpa zea*), Fall armyworm (FAW, *Spodoptera frugiperda*), and Southwestern Corn Borer (SWCB, *Diatraea grandiosella*). The assay results are shown in Table 7 below, wherein "+" indicates activity.

TABLE 7

Bioassay activity of TIC2421 and TIC3008 against Lepidopteran pests from stably transformed corn leaf tissue.

| | Insect | | |
|---|---|---|---|
| Toxin | CEW | FAW | SWCB |
| mTIC2421 | | | + |
| CTP/mTIC2421 | | + | + |
| mTIC3008 | | | |
| CTP/mTIC3008 | + | + | |

As can be seen in Table 7 above, when expressed in stably transformed corn plants mTIC2421 and mTIC3008 demonstrated activity against multiple Lepidopteran pests.

Example 4

Assay of Activity Against Western Corn Rootworm Using Stably Transformed Corn Plants Expressing TIC3008

Stably transformed corn plants transformed with the binary vectors expressing chloroplast targeted and untargeted mTIC3008 described in Example 3 above were used to assay for resistance against Western Corn Rootworm (*Diabrotica virgifera virgifera*, WCR).

The binary vectors were used to stably transform corn plants. Single T-DNA insertion events were selected and grown. The $R_0$ stably transformed plants were allowed to self-fertilize, producing $F_1$ progeny. The $F_1$ seed was planted and samples for ELISA expression measurements were taken from the young plants. The plants were transplanted to eight inch pots. Six plants were used for each treatment. Eggs from Western Corn Rootworm (*Diabrotica virgifera virgifera*, WCR) were incubated for ten days to allow hatching within four days after inoculation. At approximately V2 and V3 stage each pot was inoculated with two thousand WCR eggs. The plants were grown after infestation for approximately twenty eight days. The plants were removed from the pots with the roots being carefully washed to remove all soil. The damage to the roots was assessed using a damage rating scale of 0-3 as presented in Table 8 below. Comparison was made to the negative control to assure the assay was performed properly. Lower root damage scores indicated resistance conferred by the mTIC3008 protein to the Coleopteran pest. FIG. 2 depicts the average root damage rating for several events for mTIC3008 derived from transformations using two different constructs. Construct 1 comprises a plastid-targeted mTIC3008 coding sequence while construct 2 comprises an untargeted mTIC3008 coding sequence. As can be seen in FIG. 2, the average root damage rating of each event is lower than the negative control when mTIC3008 is expressed in F1 corn plants regardless of whether the protein is targeted to the chloroplast.

TABLE 8

$F_1$ root damage rating scores.

| Root Damage Score | Description |
|---|---|
| 0 | No visible feeding |
| 0.01-0.09 | Feeding scars and tracks |
| 0.1-0.9 | Root pruning, but less than a full node |
| 1.0-1.9 | At least a full node (or equivalent) destroyed to within 1.5 inches of plant |
| 2.0-2.9 | Two or more nodes gone |
| 3 | Three or more nodes gone |

After analysis it was determined that plants expressing both chloroplast targeted and untargeted mTIC3008 demonstrated efficacy against WCR. The insect toxin mTIC3008 provides resistance to Coleopteran pests such as WCR.

Example 5

Assay of Activity Against Lepidopteran Pests in Stably Transformed Corn Plants Expressing TIC7055

Binary plant transformation vectors comprising transgene cassettes designed to express both plastid targeted and untargeted mature TIC7055 (mTIC7055) pesticidal protein, presented as SEQ ID NO:23 are cloned using methods known in the art. The resulting vectors are used to stably transform corn plants. Tissues are harvested from the transformants and used in insect bioassay against various Lepidopteran insect pests.

Synthetic coding sequences are constructed for use in expression of the encoded protein in plants, cloned into a binary plant transformation vector, and used to transform corn plant cells. The synthetic sequences are synthesized according to methods generally described in U.S. Pat. No. 5,500,365, avoiding certain inimical problem sequences such as ATTTA and A/T rich plant polyadenylation sequences while preserving the amino acid sequence of the native Bt protein. The synthetic coding sequences encode a mature pesticidal protein which lacks a membrane transiting segment (corresponding to amino acids 2 to 37 relative to the native protein sequences) and retains an initiating methionine to permit proper translation of the mature protein. For plastid targeted protein the synthetic mature pesticidal protein coding sequence is operably linked in frame with a chloroplast targeting signal peptide coding sequence. The resulting plant transformation vectors comprise a first transgene cassette for expression of the pesticidal protein which comprises a constitutive promoter, operably linked 5' to a leader, operably linked 5' to an intron, operably linked 5' to a synthetic coding sequence, which is in turn operably linked 5' to a 3' UTR and; a second transgene cassette for the selection of transformed plant cells using glyphosate selection.

A synthetic coding sequence encodes the mature mTIC7055 pesticidal protein presented as SEQ ID NO:23. For the plastid targeted mature pesticidal protein (CTP/mTIC7055), the chloroplast targeting signal is encoded by the sequence presented as SEQ ID NO:17 and encodes the amino acid sequence presented as SEQ ID NO:18. A synthetic plastid targeted mTIC7055 (CTP/mTIC7055) coding sequence encodes the protein presented as SEQ ID NO:24.

Corn variety LH244 is transformed with the binary transformation vectors described above using an *Agrobacterium*-mediated transformation method. The transformed cells are induced to form plants by methods known in the art. Bioassays using plant leaf disks are performed analogous to those described in U.S. Pat. No. 8,344,207. A non-transformed LH244 plant is used to obtain tissue to be used as a negative control. Multiple transformation events from each binary vector are assessed against Corn earworm (CEW, *Helicoverpa zea*), Fall armyworm (FAW, *Spodoptera frugiperda*), and Southwestern Corn Borer (SWCB, *Diatraea grandiosella*). Mortality and stunting scores are derived from observations of the insects in the feeding bioassay. Mortality and/or stunting of the selected insect pest species is an indication of TIC7055 toxicity to the selected insect pest species.

Example 6

Assay of Activity Against Coleopteran Pests Using Stably Transformed Corn Plants Expressing TIC7055

Binary plant transformation vectors comprising transgene cassettes designed to express both plastid targeted and untargeted mTIC7055 pesticidal proteins are cloned using methods known in the art. The resulting vectors are used to stably transform corn plants. Pesticidal activity is assayed against Coleopteran pests feeding on the roots of the stably transformed corn plants.

The binary vectors used in assay are those as described previously in Example 8 in which plastid targeted and untargeted mTIC7055 is expressed. The binary vectors are used to stably transform corn plants. Single T-DNA insertion events are selected and grown. The $R_0$ stably transformed plants are allowed to self-fertilize, producing $F_1$ progeny. The $F_1$ seed is planted and samples for ELISA expression measurements are taken from the young plants. The plants are transplanted to eight inch pots. Six plants are used for each treatment. Eggs from *Diabrotica virgifera virgifera* (Western Corn Rootworm, WCR) or other Coleopteran species are incubated for ten days to allow hatching within four days after inoculation. At approximately V2 and V3 stage each pot is inoculated with two thousand WCR or other Coleopteran species' eggs. The plants are grown after infestation for approximately twenty eight days. The plants are removed from the pots with the roots being carefully washed to remove all soil. The damage to the roots is assessed using a damage rating scale of 0-3 with 0 indicating no damage and 3 indicating severe damage. Low root damage scores indicate resistance to the Coleopteran pest.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein, wherein:
   said pesticidal protein comprises the amino acid sequence selected from the group consisting of SEQ ID NO:8, SEQ ID NO:12, SEQ ID NO:4, and SEQ ID NO:28.

2. The recombinant nucleic acid molecule of claim 1, wherein:
   a. the recombinant nucleic acid molecule comprises a sequence that functions to express the pesticidal protein in a plant; or
   b. the recombinant nucleic acid molecule is expressed in a plant cell to produce a pesticidally effective amount of the pesticidal protein; or
   c. said recombinant nucleic acid molecule is in operable linkage to a vector, and said vector is selected from the group consisting of a plasmid, phagemid, bacmid, cosmid, and a bacterial or yeast artificial chromosome.

3. The recombinant nucleic acid molecule of claim 1, defined as present within a host cell, wherein said host cell is selected from the group consisting of a bacterial and a plant cell.

4. The recombinant nucleic acid of claim 3, wherein said plant host cell is selected from the group consisting of an alfalfa, banana, barley, bean, broccoli, cabbage, Brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

5. The recombinant nucleic acid molecule of claim 1, wherein said protein exhibits activity against an insect species of the order of Coleoptera.

6. The recombinant nucleic acid molecule of claim 5, wherein said insect species is selected from the group consisting of Western Corn Rootworm, Southern Corn Rootworm, Northern Corn Rootworm, Mexican Corn Rootworm, Brazilian Corn Rootworm, and Brazilian Corn Rootworm complex consisting of *Diabrotica viridula* and *Diabrotica speciose*.

7. The recombinant nucleic acid molecule of claim 1, wherein said protein exhibits activity against an insect species of the order of Lepidoptera.

8. The recombinant nucleic acid molecule of claim 7, wherein said insect species is selected from the group consisting of Corn earworm, and Fall armyworm.

9. A plant, or part thereof, comprising the recombinant nucleic acid molecule of claim 1.

10. The plant, or part thereof, of claim 9, wherein said plant is a monocot plant or a dicot plant.

11. The plant, or part thereof, of claim 9, wherein said plant is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

12. A seed from the plant of claim 9, wherein said seed comprises said recombinant nucleic acid molecule.

13. An insect inhibitory composition comprising the recombinant nucleic acid molecule of claim 1.

14. The insect inhibitory composition of claim 13, further comprising a nucleotide sequence encoding at least one other pesticidal agent that is different from said pesticidal protein.

15. The insect inhibitory composition of claim 14, wherein said at least one other pesticidal agent is selected from the group consisting of an insect inhibitory protein, an insect inhibitory dsRNA molecule, and an ancillary protein.

16. The insect inhibitory composition of claim 15, wherein said at least one other pesticidal agent exhibits activity against one or more pest species of the orders Lepidoptera, Coleoptera, or Hemiptera.

17. The insect inhibitory composition of claim 16, wherein said at least one other pesticidal protein is selected from the group consisting of a Cry1A, Cry1Ab, Cry1Ac, Cry1A.105, Cry1Ae, Cry1B, Cry1C, Cry1C, Cry1D, Cry1E, Cry1F, Cry1A/F chimeras, Cry1G, Cry1H, Cry 1I, Cry1J, Cry1K, Cry1L, Cry2A, Cry2Ab, Cry2Ae, Cry3, Cry3A, Cry3B, Cry4B, Cry6, Cry7, Cry8, Cry9, Cry15, Cry34, Cry35, Cry43A, Cry43B, Cry51Aa1, ET29, ET33, ET34, ET66, ET70, TIC407, TIC417, TIC431, TIC807, TIC834, TIC853, TIC900, TIC901, TIC1201, TIC1415, TIC2160, TIC3131 , TIC836, TIC860, TIC867, TIC869, TIC1100, VIP3 A, VIP3 B, VIP3Ab, AXMI-88, AXMI-97, AXMI-102, AXMI-112, AXMI-117, AXMI- 100, AXMI-115, AXMI-113, AXMI-005, AXMI134, AXMI-150, AXMI-171, AXMI- 184, AXMI-196, AXMI-204, AXMI-207, AXMI-209, AXMI-205, AXMI-218, AXMI-220, AXMI-221z, AXMI-222z, AXMI-223z, AXMI-224z, AXMI-225z, AXMI-238, AXMI-270, AXMI-279, AXMI-34, AXMI-335, AXMI-R1, DIG-3, DIG-5, DIG-10, DIG-657 and a DIG-11 protein.

18. The insect inhibitory composition of claim 13, defined as comprising a plant cell that expresses said recombinant nucleic acid molecule.

19. A method of producing seed, said method comprising:
a. planting at least a first seed according to claim 12;
b. growing a plant from the seed; and
c. harvesting seed from the plant, wherein said harvested seed comprises the recombinant nucleic acid molecule.

20. A plant resistant to insect infestation, wherein the cells of said plant comprise the recombinant nucleic acid molecule of claim 1.

21. A method for controlling a Coleopteran or Lepidopteran species pest, or pest infestation, said method comprising:
contacting the pest with an insecticidally effective amount of one or more pesticidal proteins as set forth in SEQ ID NO:8, or SEQ ID NO:12.

* * * * *

SEQUENCE LISTING

```
<160> NUMBER OF SEQ ID NOS: 30

<210> SEQ ID NO 1
<211> LENGTH: 1191
<212> TYPE: DNA
<213> ORGANISM: Bacillus thuringiensis
<220> FEATURE:
<221> NAME/KEY: misc_feature
<222> LOCATION: (1)..(1191)
<223> OTHER INFORMATION: DNA sequence derived from Bt strain CFB199510
      encoding TIC2421.
<220> FEATURE:
<221> NAME/KEY: misc_feature
<222> LOCATION: (1)..(111)
<223> OTHER INFORMATION: DNA sequence of TIC2421 encoding the secretion
      signal peptide of TIC2421.

<400> SEQUENCE: 1
atgtatacaa ataataaaat gaagtgttgg aagaaaaaat tagccaaagt tgcaccaatt      60
tgtgtgttaa gtacaggatt tttagtgggc gtagctaatc ctgcatttgc tgctagtaag     120
actccccaaa ctgttcacgc tcaagcgaaa caatctaatt tatcgactac gtctaatagt     180
aacttagttc atatcggtga tgatttaaat caaagaatcc atgatgctgt gaaaaataaa     240
cccgatttat ttttgtatag atatcttagg gatgatagag gaagaacgaa tgtgcggatg     300
aatgatatgc ctcaaagtga caacagtggt tataactttg taatgaatag cttacaatac     360
```

-continued

```
ggaaaagtta cgattaacaa tggatataat atcgattgga atcaaagaga atatgtcggt    420
ggagatatca aggtaacggg taaacaagat agcataggtg gattgcatag ctttacaata    480
ggaacttttc ataacactga agatattgaa caaacggcta ctacgcaaaa agaaacctat    540
caaacaacag atagttttac ctattcaaat agtgagggtg tcaagttagg attgacagaa    600
tctataaaag caactgctgg tgtacctttt gttatagcag gcgaagagac aaccacactc    660
tcaagtgagt tttcatataa tcatacctct tcaaatacat cgacgaactc acatacaatt    720
gaatttccat cgcagactat taaagtcaaa ccgcatggaa ctacacttta cacgggtgag    780
gtaaaacaaa tgaatttttc tggagattac tctgggacag tgaaattatc aacaaaggat    840
gtttcttttg caataacgga ttcgggaggt cattggggag atattatcgc tgcgccgggt    900
gaagaggagc atttttata taatatattt aaatactccg gtcatccaat tccttcagat    960
attcgtttag atgatgaaaa tagaacggtt gttgttgata attcatccat tcattttaca   1020
ggaaaactag gttttaacat ggaggcaaca tggaaattca tccctgatga tcctaaaaaa   1080
ccaagtgtta caataccaaa tgatgtatat ttaaaagaac aagcttctgg gaatattagc   1140
aagtacattg accaattaat acaaactaaa atgaaatcta tgcatcaata a             1191
```

<210> SEQ ID NO 2
<211> LENGTH: 396
<212> TYPE: PRT
<213> ORGANISM: Bacillus thuringiensis
<220> FEATURE:
<221> NAME/KEY: MISC_FEATURE
<222> LOCATION: (1)..(396)
<223> OTHER INFORMATION: Amino acid sequence of TIC2421.
<220> FEATURE:
<221> NAME/KEY: MISC_FEATURE
<222> LOCATION: (1)..(37)
<223> OTHER INFORMATION: Secretion signal amino acid sequence.

<400> SEQUENCE: 2

```
Met Tyr Thr Asn Asn Lys Met Lys Cys Trp Lys Lys Lys Leu Ala Lys
1               5                   10                  15

Val Ala Pro Ile Cys Val Leu Ser Thr Gly Phe Leu Val Gly Val Ala
            20                  25                  30

Asn Pro Ala Phe Ala Ala Ser Lys Thr Pro Gln Thr Val His Ala Gln
        35                  40                  45

Ala Lys Gln Ser Asn Leu Ser Thr Thr Ser Asn Ser Asn Leu Val His
    50                  55                  60

Ile Gly Asp Asp Leu Asn Gln Arg Ile His Asp Ala Val Lys Asn Lys
65                  70                  75                  80

Pro Asp Leu Phe Leu Tyr Arg Tyr Leu Arg Asp Asp Arg Gly Arg Thr
                85                  90                  95

Asn Val Arg Met Asn Asp Met Pro Gln Ser Asp Asn Ser Gly Tyr Asn
            100                 105                 110

Phe Val Met Asn Ser Leu Gln Tyr Gly Lys Val Thr Ile Asn Asn Gly
        115                 120                 125

Tyr Asn Ile Asp Trp Asn Gln Arg Glu Tyr Val Gly Gly Asp Ile Lys
    130                 135                 140

Val Thr Gly Lys Gln Asp Ser Ile Gly Gly Leu His Ser Phe Thr Ile
145                 150                 155                 160

Gly Thr Phe His Asn Thr Glu Asp Ile Glu Gln Thr Ala Thr Thr Gln
                165                 170                 175

Lys Glu Thr Tyr Gln Thr Thr Asp Ser Phe Thr Tyr Ser Asn Ser Glu
```

```
                180             185                 190
Gly Val Lys Leu Gly Leu Thr Glu Ser Ile Lys Ala Thr Ala Gly Val
            195                 200                 205

Pro Phe Val Ile Ala Gly Glu Glu Thr Thr Thr Leu Ser Ser Glu Phe
            210                 215                 220

Ser Tyr Asn His Thr Ser Ser Asn Thr Ser Thr Asn Ser His Thr Ile
225                 230                 235                 240

Glu Phe Pro Ser Gln Thr Ile Lys Val Lys Pro His Gly Thr Thr Leu
                245                 250                 255

Tyr Thr Gly Glu Val Lys Gln Met Asn Phe Ser Gly Asp Tyr Ser Gly
            260                 265                 270

Thr Val Lys Leu Ser Thr Lys Asp Val Ser Phe Ala Ile Thr Asp Ser
            275                 280                 285

Gly Gly His Trp Gly Asp Ile Ile Ala Ala Pro Gly Glu Glu His
            290                 295                 300

Phe Leu Tyr Asn Ile Phe Lys Tyr Ser Gly His Pro Ile Pro Ser Asp
305                 310                 315                 320

Ile Arg Leu Asp Asp Glu Asn Arg Thr Val Val Asp Asn Ser Ser
                325                 330                 335

Ile His Phe Thr Gly Lys Leu Gly Phe Asn Met Glu Ala Thr Trp Lys
            340                 345                 350

Phe Ile Pro Asp Asp Pro Lys Lys Pro Ser Val Thr Ile Pro Asn Asp
            355                 360                 365

Val Tyr Leu Lys Glu Gln Ala Ser Gly Asn Ile Ser Lys Tyr Ile Asp
            370                 375                 380

Gln Leu Ile Gln Thr Lys Met Lys Ser Met His Gln
385                 390                 395
```

<210> SEQ ID NO 3
<211> LENGTH: 1203
<212> TYPE: DNA
<213> ORGANISM: Bacillus thuringiensis
<220> FEATURE:
<221> NAME/KEY: misc_feature
<222> LOCATION: (1)..(1203)
<223> OTHER INFORMATION: DNA sequence derived from Bt strain CFB005050 encoding TIC3008.
<220> FEATURE:
<221> NAME/KEY: misc_feature
<222> LOCATION: (1)..(111)
<223> OTHER INFORMATION: DNA sequence of TIC3008 encoding the secretion signal peptide of TIC3008.

<400> SEQUENCE: 3

```
atgaaaacta ataaccaaat tagagatcgc aagaaaaaaa tagccaaaat tgtacccatt      60
tgtgtaataa gtacaggatt tttagttgga ctagtgaatc ctgcatttgc aaaaactacc     120
gaatctaagc tatcttctca acaaactatc catgaccaag gcataaagtc tacatccctg     180
gccacttcta atgacaatat taatttgtat catattggag atgacttaaa tcaaagaata     240
tatgacgctg tcaagaatag accagattta tttgtatacc atcatgtcaa aggagaatct     300
ggtagaaatg aaaaaatcag tgatatggac aaaagtttaa caaatggcta tatcgttgta     360
atgaataatc tgaaataccc tggagttact atcaataacg gatataatat tgattggaat     420
caacgtgaat acgttggggg cgatataaag gtgacaggaa aacaagatag tgtagacgga     480
ctgcatagtt ttaccttagg aactttccac aatactgaaa atatcgaaca aattgctacg     540
acacaaaaag aatcctatca aaccaccgat agttttacat attcaactag taaaggggtt     600
```

```
aaattaggat taaccgaatc cctaaaagca actgcaggtg ttccattaat agtaaatgga     660
gaagaaacga caacactttc aactgagttt tcgtataatc aaacttcttc aaatacagca     720
actaattcac atacaattga attcccatca cagactatta aagtgaaacc gcacggaact     780
acgatttata ttggtgaagt gaaacagtta aaattctctg gagattattc tggtaccaca     840
aagcttacaa cacaagatgt ctcttttccg atagtggatt cagaaggtca ttggggagat     900
gtaattgctg ctccaggtga gaagaacat tttttatata atatatttaa gtattctggt     960
cactcaatcc cagctgatat tcgcttagat gacgcaagca aaactgttgt ggtggataat    1020
tcttccattc attttacagg taaattaggt ttcaacatgg aagctacttg gaagttcata    1080
ccagatgatc cacaaaaacc agccgtaacg attcctcacg atgtatatat gaaagaacaa    1140
gcatcaggga atataagtaa atatattgat caattgatat aaataaaac gcaagctaaa    1200 taa                                                                  1203
```

<210> SEQ ID NO 4
<211> LENGTH: 400
<212> TYPE: PRT
<213> ORGANISM: Bacillus thuringiensis
<220> FEATURE:
<221> NAME/KEY: MISC_FEATURE
<222> LOCATION: (1)..(400)
<223> OTHER INFORMATION: Amino acid sequence of TIC3008.
<220> FEATURE:
<221> NAME/KEY: MISC_FEATURE
<222> LOCATION: (1)..(37)
<223> OTHER INFORMATION: Secretion signal amino acid sequence.

<400> SEQUENCE: 4

```
Met Lys Thr Asn Asn Gln Ile Arg Asp Arg Lys Lys Ile Ala Lys
1               5                   10                  15

Ile Val Pro Ile Cys Val Ile Ser Thr Gly Phe Leu Val Gly Leu Val
            20                  25                  30

Asn Pro Ala Phe Ala Lys Thr Thr Glu Ser Lys Leu Ser Ser Gln Gln
        35                  40                  45

Thr Ile His Asp Gln Gly Ile Lys Ser Thr Ser Leu Ala Thr Ser Asn
    50                  55                  60

Asp Asn Ile Asn Leu Tyr His Ile Gly Asp Asp Leu Asn Gln Arg Ile
65                  70                  75                  80

Tyr Asp Ala Val Lys Asn Arg Pro Asp Leu Phe Val Tyr His His Val
                85                  90                  95

Lys Gly Glu Ser Gly Arg Asn Glu Lys Ile Ser Asp Met Asp Lys Ser
            100                 105                 110

Leu Thr Asn Gly Tyr Ile Val Val Met Asn Asn Leu Lys Tyr Pro Gly
        115                 120                 125

Val Thr Ile Asn Asn Gly Tyr Asn Ile Asp Trp Asn Gln Arg Glu Tyr
    130                 135                 140

Val Gly Gly Asp Ile Lys Val Thr Gly Lys Gln Asp Ser Val Asp Gly
145                 150                 155                 160

Leu His Ser Phe Thr Leu Gly Thr Phe His Asn Thr Glu Asn Ile Glu
                165                 170                 175

Gln Ile Ala Thr Thr Gln Lys Glu Ser Tyr Gln Thr Thr Asp Ser Phe
            180                 185                 190

Thr Tyr Ser Thr Ser Lys Gly Val Lys Leu Gly Leu Thr Glu Ser Leu
        195                 200                 205

Lys Ala Thr Ala Gly Val Pro Leu Ile Val Asn Gly Glu Glu Thr Thr
    210                 215                 220
```

```
Thr Leu Ser Thr Glu Phe Ser Tyr Asn Gln Thr Ser Ser Asn Thr Ala
225                 230                 235                 240

Thr Asn Ser His Thr Ile Glu Phe Pro Ser Gln Thr Ile Lys Val Lys
            245                 250                 255

Pro His Gly Thr Thr Ile Tyr Ile Gly Glu Val Lys Gln Leu Lys Phe
        260                 265                 270

Ser Gly Asp Tyr Ser Gly Thr Thr Lys Leu Thr Thr Gln Asp Val Ser
    275                 280                 285

Phe Pro Ile Val Asp Ser Glu Gly His Trp Gly Asp Val Ile Ala Ala
290                 295                 300

Pro Gly Glu Lys Glu His Phe Leu Tyr Asn Ile Phe Lys Tyr Ser Gly
305                 310                 315                 320

His Ser Ile Pro Ala Asp Ile Arg Leu Asp Asp Ala Ser Lys Thr Val
            325                 330                 335

Val Val Asp Asn Ser Ser Ile His Phe Thr Gly Lys Leu Gly Phe Asn
        340                 345                 350

Met Glu Ala Thr Trp Lys Phe Ile Pro Asp Asp Pro Gln Lys Pro Ala
    355                 360                 365

Val Thr Ile Pro His Asp Val Tyr Met Lys Glu Gln Ala Ser Gly Asn
370                 375                 380

Ile Ser Lys Tyr Ile Asp Gln Leu Ile Leu Asn Lys Thr Gln Ala Lys
385                 390                 395                 400
```

<210> SEQ ID NO 5
<211> LENGTH: 1083
<212> TYPE: DNA
<213> ORGANISM: Artificial
<220> FEATURE:
<223> OTHER INFORMATION: Synthetic coding sequence encoding mTIC2421
      designed for expression in plants, derived from the Bacillus
      thuringiensis coding sequence encoding TIC2421.

<400> SEQUENCE: 5

```
atggcgtcaa agacgccgca gacggtgcac gcccaggcga acagagtaa cctgtcgacc      60
acgagcaact cgaacctcgt acacatcggc gacgacctca accagcgtat ccacgacgcc    120
gtcaagaaca gcccgacct cttcctctac cgctacctcc gggacgaccg cggccggacc     180
aatgtccgga tgaacgacat gcctcagtcg gataactccg ggtacaactt cgtcatgaac    240
agccttcagt acggcaaggt gaccattaac aacggctaca catcgactg gaatcagcgc    300
gaatacgtcg gcggcgacat caaggtcacc gggaagcaag acagcatcgg aggcctgcat    360
tcctttacaa ttgggacctt ccataacacg gaggacatcg agcagacggc gacgacgcag    420
aaggagacgt accagaccac ggattctttc acctacagca attctgaagg tgttaaactt    480
ggcctgaccg agtcgataaa ggccacagcc ggcgtccctt cgtcatcgc cggcgaggag    540
acgacgacgc tcagtagcga gttctcttac aaccacacgt cgagcaacac gtcgactaac    600
tcccacacca tcgagttccc gagccagacc atcaaggtca gccgcacgg gaccacgctc    660
tacacgggcg aggtcaagca gatgaacttc tcgggtgact acagcgggac agtgaagctg    720
tccacgaagg atgtctcctt cgcgatcacg gactcgggcg gccactgggg cgacataatc    780
gcggcgcccg gcgaggagga gcacttcctg tacaacatct tcaagtactc cggccatccc    840
attccgagcg acatccggct cgacgatgag aatcgaacgg tggtcgtcga caacagctcc    900
atccacttca ccggcaagct gggcttcaac atggaggcaa cctggaaatt cataccccgac    960
gatccgaaga gccctcggt gacgatacc aacgacgtct acttgaaaga gcaagccagc    1020
```
gggaacatca gcaagtacat cgaccagttg atccagacca agatgaagag tatgcaccag    1080
tag    1083

<210> SEQ ID NO 6
<211> LENGTH: 360
<212> TYPE: PRT
<213> ORGANISM: Artificial
<220> FEATURE:
<223> OTHER INFORMATION: Amino acid sequence translation from a
      synthetic DNA sequence encoding mTIC2421.

<400> SEQUENCE: 6

Met Ala Ser Lys Thr Pro Gln Thr Val His Ala Gln Ala Lys Gln Ser
1               5                   10                  15

Asn Leu Ser Thr Thr Ser Asn Ser Asn Leu Val His Ile Gly Asp Asp
            20                  25                  30

Leu Asn Gln Arg Ile His Asp Ala Val Lys Asn Lys Pro Asp Leu Phe
        35                  40                  45

Leu Tyr Arg Tyr Leu Arg Asp Asp Arg Gly Arg Thr Asn Val Arg Met
    50                  55                  60

Asn Asp Met Pro Gln Ser Asp Asn Ser Gly Tyr Asn Phe Val Met Asn
65                  70                  75                  80

Ser Leu Gln Tyr Gly Lys Val Thr Ile Asn Asn Gly Tyr Asn Ile Asp
                85                  90                  95

Trp Asn Gln Arg Glu Tyr Val Gly Gly Asp Ile Lys Val Thr Gly Lys
            100                 105                 110

Gln Asp Ser Ile Gly Gly Leu His Ser Phe Thr Ile Gly Thr Phe His
        115                 120                 125

Asn Thr Glu Asp Ile Glu Gln Thr Ala Thr Thr Gln Lys Glu Thr Tyr
    130                 135                 140

Gln Thr Thr Asp Ser Phe Thr Tyr Ser Asn Ser Glu Gly Val Lys Leu
145                 150                 155                 160

Gly Leu Thr Glu Ser Ile Lys Ala Thr Ala Gly Val Pro Phe Val Ile
                165                 170                 175

Ala Gly Glu Glu Thr Thr Thr Leu Ser Ser Gly Phe Ser Tyr Asn His
            180                 185                 190

Thr Ser Ser Asn Thr Ser Thr Asn Ser His Thr Ile Glu Phe Pro Ser
        195                 200                 205

Gln Thr Ile Lys Val Lys Pro His Gly Thr Thr Leu Tyr Thr Gly Glu
    210                 215                 220

Val Lys Gln Met Asn Phe Ser Gly Asp Tyr Ser Gly Thr Val Lys Leu
225                 230                 235                 240

Ser Thr Lys Asp Val Ser Phe Ala Ile Thr Asp Ser Gly Gly His Trp
                245                 250                 255

Gly Asp Ile Ile Ala Ala Pro Gly Glu Glu His Phe Leu Tyr Asn
            260                 265                 270

Ile Phe Lys Tyr Ser Gly His Pro Ile Pro Ser Asp Ile Arg Leu Asp
        275                 280                 285

Asp Glu Asn Arg Thr Val Val Val Asp Asn Ser Ser Ile His Phe Thr
    290                 295                 300

Gly Lys Leu Gly Phe Asn Met Glu Ala Thr Trp Lys Phe Ile Pro Asp
305                 310                 315                 320

Asp Pro Lys Lys Pro Ser Val Thr Ile Pro Asn Asp Val Tyr Leu Lys
                325                 330                 335

```
Glu Gln Ala Ser Gly Asn Ile Ser Lys Tyr Ile Asp Gln Leu Ile Gln
        340                 345                 350

Thr Lys Met Lys Ser Met His Gln
        355                 360

<210> SEQ ID NO 7
<211> LENGTH: 1095
<212> TYPE: DNA
<213> ORGANISM: Artificial
<220> FEATURE:
<223> OTHER INFORMATION: Synthetic coding sequence encoding mTIC3008
      designed for expression in plants, derived from the Bacillus
      thuringiensis coding sequence encoding TIC3008.

<400> SEQUENCE: 7
atgaagacga ccgagagcaa gctgagcagc cagcagacca ttcacgacca gggcattaag       60
agcacctccc tcgcgacctc caacgataac atcaatctct accacatcgg tgacgacctt      120
aaccagcgca tctacgacgc cgtgaagaac cgcccagacc tgttcgtgta ccaccacgtc      180
aaaggcgagt cgggccggaa cgagaagatc tctgacatgg acaagtcttt gaccaacggg      240
tacatcgtgg tgatgaataa cctaaagtat cctggcgtca cgatcaacaa cggctacaac      300
atcgactgga accagcgcga gtacgtgggc ggcgacatca aggtcacggg caagcaagac      360
tcagttgatg ggttgcacag cttcaccctc gggaccttcc acaacacgga gaacatcgag      420
caaatcgcga ccacccagaa ggagtcatac cagaccaccg actcgttcac ttactctacc      480
tcgaagggcg tgaagttggg tctcaccgag agcctcaagg cgaccgcggg cgtcccgctc      540
atcgtcaacg gcgaggagac cacgacgctg tctacggagt ctcctacaa ccagacaagc       600 tcgaacaccg cgaccaactc tcacacgatc gagtttccct cgcaaaccat caaggtcaag      660
cctcacggca ccgcgatcta catcggcgag gtcaagcagt tgaagttctc gggcgactac      720
tcgggcacga cgaagctcac cacgcaagac gtgtcctttc ccatcgtcga ctccgagggt      780
cactggggcg acgtgatcgc cgcgcccggc gagaaggagc acttcctgta caacatcttc      840
aagtactctg ccacagcat ccctgctgac atccgcctgg acgacgcttc gaagaccgtg       900
gtcgtcgaca cagtagcat ccacttcacg ggcaagctcg gcttcaacat ggaggctacc       960
tggaagttca tcccggacga ccctcagaag cccgcggtga ctatccctca cgacgtgtac     1020
atgaaggaac aggcgtctgg caacatctcg aagtacatcg accagctcat cctgaacaag     1080
acccaggcca agtag                                                      1095

<210> SEQ ID NO 8
<211> LENGTH: 364
<212> TYPE: PRT
<213> ORGANISM: Artificial
<220> FEATURE:
<223> OTHER INFORMATION: Amino acid sequence translation from a
      synthetic DNA sequence encoding mTIC3008.

<400> SEQUENCE: 8

Met Lys Thr Thr Glu Ser Lys Leu Ser Ser Gln Gln Thr Ile His Asp
1               5                   10                  15

Gln Gly Ile Lys Ser Thr Ser Leu Ala Thr Ser Asn Asp Asn Ile Asn
            20                  25                  30

Leu Tyr His Ile Gly Asp Asp Leu Asn Gln Arg Ile Tyr Asp Ala Val
        35                  40                  45

Lys Asn Arg Pro Asp Leu Phe Val Tyr His Val Lys Gly Glu Ser
    50                  55                  60
```

Gly Arg Asn Glu Lys Ile Ser Asp Met Asp Lys Ser Leu Thr Asn Gly
 65                  70                  75                  80

Tyr Ile Val Val Met Asn Asn Leu Lys Tyr Pro Gly Val Thr Ile Asn
                 85                  90                  95

Asn Gly Tyr Asn Ile Asp Trp Asn Gln Arg Glu Tyr Val Gly Gly Asp
            100                 105                 110

Ile Lys Val Thr Gly Lys Gln Asp Ser Val Asp Gly Leu His Ser Phe
        115                 120                 125

Thr Leu Gly Thr Phe His Asn Thr Glu Asn Ile Glu Gln Ile Ala Thr
    130                 135                 140

Thr Gln Lys Glu Ser Tyr Gln Thr Thr Asp Ser Phe Thr Tyr Ser Thr
145                 150                 155                 160

Ser Lys Gly Val Lys Leu Gly Leu Thr Glu Ser Leu Lys Ala Thr Ala
                165                 170                 175

Gly Val Pro Leu Ile Val Asn Gly Glu Glu Thr Thr Thr Leu Ser Thr
            180                 185                 190

Glu Phe Ser Tyr Asn Gln Thr Ser Ser Asn Thr Ala Thr Asn Ser His
        195                 200                 205

Thr Ile Glu Phe Pro Ser Gln Thr Ile Lys Val Lys Pro His Gly Thr
    210                 215                 220

Thr Ile Tyr Ile Gly Glu Val Lys Gln Leu Lys Phe Ser Gly Asp Tyr
225                 230                 235                 240

Ser Gly Thr Thr Lys Leu Thr Thr Gln Asp Val Ser Phe Pro Ile Val
                245                 250                 255

Asp Ser Glu Gly His Trp Gly Asp Val Ile Ala Ala Pro Gly Glu Lys
            260                 265                 270

Glu His Phe Leu Tyr Asn Ile Phe Lys Tyr Ser Gly His Ser Ile Pro
        275                 280                 285

Ala Asp Ile Arg Leu Asp Asp Ala Ser Lys Thr Val Val Val Asp Asn
    290                 295                 300

Ser Ser Ile His Phe Thr Gly Lys Leu Gly Phe Asn Met Glu Ala Thr
305                 310                 315                 320

Trp Lys Phe Ile Pro Asp Asp Pro Gln Lys Pro Ala Val Thr Ile Pro
                325                 330                 335

His Asp Val Tyr Met Lys Glu Gln Ala Ser Gly Asn Ile Ser Lys Tyr
            340                 345                 350

Ile Asp Gln Leu Ile Leu Asn Lys Thr Gln Ala Lys
        355                 360

<210> SEQ ID NO 9
<211> LENGTH: 1308
<212> TYPE: DNA
<213> ORGANISM: Artificial
<220> FEATURE:
<223> OTHER INFORMATION: Synthetic coding sequence encoding plastid
      targeted CTP/mTIC2421 designed for expression in plants.

<400> SEQUENCE: 9
atggcggctc tggccacttc ccagctcgcc accacccgcg ccggcttcgg cctcggcgac      60
gcctcctcct ccatgttccg ccccggcgtc cagggcctca ggggctcccg ggcctcctcc     120
ccggcggcca cgctcagcgt gcggaccagc gcgcgcgccg cgcccaggca gcagcaccgc     180
cgggcgcagc gcggcgccag gttcccctcc ctcgtcgtct cgccatggc gtcaaagacg      240 ccgcagacgg tgcacgccca ggcgaaacag agtaacctgt cgaccacgag caactcgaac     300
ctcgtacaca tcggcgacga cctcaaccag cgtatccacg acgccgtcaa gaacaagccc     360

-continued

```
gacctcttcc tctaccgcta cctccgggac gaccgcggcc ggaccaatgt ccggatgaac      420
gacatgcctc agtcggataa ctccgggtac aacttcgtca tgaacagcct tcagtacggc      480
aaggtgacca ttaacaacgg ctacaacatc gactggaatc agcgcgaata cgtcggcggc      540
gacatcaagg tcaccgggaa gcaagacagc atcggaggcc tgcattcctt tacaattggg      600
accttccata cacggagga catcgagcag acggcgacga cgcagaagga cgtaccag       660 accacggatt ctttcaccta cagcaattct gaaggtgtta aacttggcct gaccgagtcg      720
ataaaggcca cagccggcgt ccctttcgtc atcgccggcg aggagacgac gacgctcagt      780
agcgagttct cttacaacca cacgtcgagc aacacgtcga ctaactccca caccatcgag      840
ttcccgagcc agaccatcaa ggtcaagccg cacgggacca cgctctacac gggcgaggtc      900
aagcagatga acttctcggg tgactacagc gggacagtga agctgtccac gaaggatgtc      960
tccttcgcga tcacggactc gggcggccac tggggcgaca taatcgcggc gcccggcgag     1020
gaggagcact tcctgtacaa catcttcaag tactccggcc atcccattcc gagcgacatc     1080
cggctcgacg atgagaatcg aacggtggtc gtcgacaaca gctccatcca cttcaccggc     1140
aagctgggct tcaacatgga ggcaacctgg aaattcatac ccgacgatcc gaagaagccc     1200
tcggtgacga tacccaacga cgtctacttg aaagagcaag ccagcgggaa catcagcaag     1260
tacatcgacc agttgatcca gaccaagatg aagagtatgc accagtag               1308
```

<210> SEQ ID NO 10
<211> LENGTH: 435
<212> TYPE: PRT
<213> ORGANISM: Artificial
<220> FEATURE:
<223> OTHER INFORMATION: Amino acid sequence translation from a
      synthetic DNA sequence encoding CTP/mTIC2421.

<400> SEQUENCE: 10

```
Met Ala Ala Leu Ala Thr Ser Gln Leu Ala Thr Thr Arg Ala Gly Phe
1               5                   10                  15

Gly Leu Gly Asp Ala Ser Ser Ser Met Phe Arg Pro Gly Val Gln Gly
            20                  25                  30

Leu Arg Gly Ser Arg Ala Ser Ser Pro Ala Ala Thr Leu Ser Val Arg
        35                  40                  45

Thr Ser Ala Arg Ala Ala Pro Arg Gln Gln His Arg Arg Ala Gln Arg
    50                  55                  60

Gly Ala Arg Phe Pro Ser Leu Val Val Cys Ala Met Ala Ser Lys Thr
65                  70                  75                  80

Pro Gln Thr Val His Ala Gln Ala Lys Gln Ser Asn Leu Ser Thr Thr
                85                  90                  95

Ser Asn Ser Asn Leu Val His Ile Gly Asp Asp Leu Asn Gln Arg Ile
            100                 105                 110

His Asp Ala Val Lys Asn Lys Pro Asp Leu Phe Leu Tyr Arg Tyr Leu
        115                 120                 125

Arg Asp Asp Arg Gly Arg Thr Asn Val Arg Met Asn Asp Met Pro Gln
    130                 135                 140

Ser Asp Asn Ser Gly Tyr Asn Phe Val Met Asn Ser Leu Gln Tyr Gly
145                 150                 155                 160

Lys Val Thr Ile Asn Asn Gly Tyr Asn Ile Asp Trp Asn Gln Arg Glu
                165                 170                 175

Tyr Val Gly Gly Asp Ile Lys Val Thr Gly Lys Gln Asp Ser Ile Gly
            180                 185                 190
```

Gly Leu His Ser Phe Thr Ile Gly Thr Phe His Asn Thr Glu Asp Ile
        195                 200                 205

Glu Gln Thr Ala Thr Thr Gln Lys Glu Thr Tyr Gln Thr Thr Asp Ser
    210                 215                 220

Phe Thr Tyr Ser Asn Ser Glu Gly Val Lys Leu Gly Leu Thr Glu Ser
225                 230                 235                 240

Ile Lys Ala Thr Ala Gly Val Pro Phe Val Ile Ala Gly Glu Thr
                245                 250                 255

Thr Thr Leu Ser Ser Glu Phe Ser Tyr Asn His Thr Ser Ser Asn Thr
            260                 265                 270

Ser Thr Asn Ser His Thr Ile Glu Phe Pro Ser Gln Thr Ile Lys Val
        275                 280                 285

Lys Pro His Gly Thr Thr Leu Tyr Thr Gly Glu Val Lys Gln Met Asn
    290                 295                 300

Phe Ser Gly Asp Tyr Ser Gly Thr Val Lys Leu Ser Thr Lys Asp Val
305                 310                 315                 320

Ser Phe Ala Ile Thr Asp Ser Gly Gly His Trp Gly Asp Ile Ile Ala
                325                 330                 335

Ala Pro Gly Glu Glu His Phe Leu Tyr Asn Ile Phe Lys Tyr Ser
            340                 345                 350

Gly His Pro Ile Pro Ser Asp Ile Arg Leu Asp Asp Glu Asn Arg Thr
        355                 360                 365

Val Val Val Asp Asn Ser Ser Ile His Phe Thr Gly Lys Leu Gly Phe
    370                 375                 380

Asn Met Glu Ala Thr Trp Lys Phe Ile Pro Asp Asp Pro Lys Lys Pro
385                 390                 395                 400

Ser Val Thr Ile Pro Asn Asp Val Tyr Leu Lys Glu Gln Ala Ser Gly
                405                 410                 415

Asn Ile Ser Lys Tyr Ile Asp Gln Leu Ile Gln Thr Lys Met Lys Ser
            420                 425                 430

Met His Gln
        435

<210> SEQ ID NO 11
<211> LENGTH: 1320
<212> TYPE: DNA
<213> ORGANISM: Artificial
<220> FEATURE:
<223> OTHER INFORMATION: Synthetic coding sequence encoding plastid
      targeted CTP/mTIC3080 designed for expression in plants.

<400> SEQUENCE: 11
atggcggctc tggccacttc ccagctcgcc accacccgcg ccggcttcgg cctcggcgac      60
gcctcctcct ccatgttccg ccccggcgtc cagggcctca ggggctcccg ggcctcctcc     120
ccggcggcca cgctcagcgt gcggaccagc gcgcgcgccg cgcccaggca gcagcaccgc     180
cgggcgcagc gcggcgccag gttcccctcc ctcgtcgtct cgccatgaa gacgaccgag      240 agcaagctga gcagccagca gaccattcac gaccagggca ttaagagcac ctccctcgcg     300
acctccaacg ataacatcaa tctctaccac atcggtgacg accttaacca gcgcatctac     360
gacgccgtga agaaccgccc agacctgttc gtgtaccacc acgtcaaagg cgagtcgggc     420
cggaacgaga agatctctga catggacaag tctttgacca acgggtacat cgtggtgatg     480
aataacctaa agtatcctgg cgtcacgatc aacaacggct acaacatcga ctggaaccag     540
cgcgagtacg tgggcggcga catcaaggtc acgggcaagc aagactcagt tgatgggttg     600

```
cacagcttca ccctcgggac cttccacaac acggagaaca tcgagcaaat cgcgaccacc      660
cagaaggagt cataccagac caccgactcg ttcacttact ctacctcgaa gggcgtgaag      720
ttgggtctca ccgagagcct caaggcgacc gcgggcgtcc cgctcatcgt caacggcgag      780
gagaccacga cgctgtctac ggagttctcc tacaaccaga caagctcgaa caccgcgacc      840
aactctcaca cgatcgagtt tccctcgcaa accatcaagg tcaagcctca cggcaccacg      900
atctacatcg gcgaggtcaa gcagttgaag ttctcgggcg actactcggg cacgacgaag      960
ctcaccacgc aagacgtgtc ctttcccatc gtcgactccg agggtcactg gggcgacgtg     1020
atcgccgcgc ccggcgagaa ggagcacttc ctgtacaaca tcttcaagta ctctggccac     1080
agcatccctg ctgacatccg cctggacgac gcttcgaaga ccgtggtcgt cgacaacagt     1140
agcatccact tcacgggcaa gctcggcttc aacatggagg ctacctggaa gttcatcccg     1200
gacgaccctc agaagcccgc ggtgactatc cctcacgacg tgtacatgaa ggaacaggcg     1260
tctggcaaca tctcgaagta catcgaccag ctcatcctga acaagaccca ggccaagtag     1320
```

<210> SEQ ID NO 12
<211> LENGTH: 439
<212> TYPE: PRT
<213> ORGANISM: Artificial
<220> FEATURE:
<223> OTHER INFORMATION: Amino acid sequence translation from a
      synthetic DNA sequence encoding CTP/mTIC3008.

<400> SEQUENCE: 12

```
Met Ala Ala Leu Ala Thr Ser Gln Leu Ala Thr Thr Arg Ala Gly Phe
1               5                   10                  15

Gly Leu Gly Asp Ala Ser Ser Met Phe Arg Pro Gly Val Gln Gly
            20                  25                  30

Leu Arg Gly Ser Arg Ala Ser Ser Pro Ala Ala Thr Leu Ser Val Arg
        35                  40                  45

Thr Ser Ala Arg Ala Ala Pro Arg Gln Gln His Arg Arg Ala Gln Arg
    50                  55                  60

Gly Ala Arg Phe Pro Ser Leu Val Val Cys Ala Met Lys Thr Thr Glu
65                  70                  75                  80

Ser Lys Leu Ser Ser Gln Gln Thr Ile His Asp Gln Gly Ile Lys Ser
                85                  90                  95

Thr Ser Leu Ala Thr Ser Asn Asp Asn Ile Asn Leu Tyr His Ile Gly
            100                 105                 110

Asp Asp Leu Asn Gln Arg Ile Tyr Asp Ala Val Lys Asn Arg Pro Asp
        115                 120                 125

Leu Phe Val Tyr His His Val Lys Gly Glu Ser Gly Arg Asn Glu Lys
    130                 135                 140

Ile Ser Asp Met Asp Lys Ser Leu Thr Asn Gly Tyr Ile Val Val Met
145                 150                 155                 160

Asn Asn Leu Lys Tyr Pro Gly Val Thr Ile Asn Gly Tyr Asn Ile
                165                 170                 175

Asp Trp Asn Gln Arg Glu Tyr Val Gly Gly Asp Ile Lys Val Thr Gly
            180                 185                 190

Lys Gln Asp Ser Val Asp Gly Leu His Ser Phe Thr Leu Gly Thr Phe
        195                 200                 205

His Asn Thr Glu Asn Ile Glu Gln Ile Ala Thr Thr Gln Lys Glu Ser
    210                 215                 220

Tyr Gln Thr Thr Asp Ser Phe Thr Tyr Ser Thr Ser Lys Gly Val Lys
```

```
                225                 230                 235                 240
Leu Gly Leu Thr Glu Ser Leu Lys Ala Thr Ala Gly Val Pro Leu Ile
                245                 250                 255

Val Asn Gly Glu Glu Thr Thr Thr Leu Ser Thr Glu Phe Ser Tyr Asn
                260                 265                 270

Gln Thr Ser Ser Asn Thr Ala Thr Asn Ser His Thr Ile Glu Phe Pro
                275                 280                 285

Ser Gln Thr Ile Lys Val Lys Pro His Gly Thr Thr Ile Tyr Ile Gly
                290                 295                 300

Glu Val Lys Gln Leu Lys Phe Ser Gly Asp Tyr Ser Gly Thr Thr Lys
305                 310                 315                 320

Leu Thr Thr Gln Asp Val Ser Phe Pro Ile Val Asp Ser Glu Gly His
                325                 330                 335

Trp Gly Asp Val Ile Ala Ala Pro Gly Glu Lys Glu His Phe Leu Tyr
                340                 345                 350

Asn Ile Phe Lys Tyr Ser Gly His Ser Ile Pro Ala Asp Ile Arg Leu
                355                 360                 365

Asp Asp Ala Ser Lys Thr Val Val Val Asp Asn Ser Ser Ile His Phe
            370                 375                 380

Thr Gly Lys Leu Gly Phe Asn Met Glu Ala Thr Trp Lys Phe Ile Pro
385                 390                 395                 400

Asp Asp Pro Gln Lys Pro Ala Val Thr Ile Pro His Asp Val Tyr Met
                405                 410                 415

Lys Glu Gln Ala Ser Gly Asn Ile Ser Lys Tyr Ile Asp Gln Leu Ile
                420                 425                 430

Leu Asn Lys Thr Gln Ala Lys
            435

<210> SEQ ID NO 13
<211> LENGTH: 111
<212> TYPE: DNA
<213> ORGANISM: Bacillus thuringiensis
<220> FEATURE:
<221> NAME/KEY: misc_feature
<222> LOCATION: (1)..(111)
<223> OTHER INFORMATION: DNA sequence encoding the secretion signal
      peptide of TIC2421.

<400> SEQUENCE: 13
atgtatacaa ataataaaat gaagtgttgg aagaaaaaat tagccaaagt tgcaccaatt      60
tgtgtgttaa gtacaggatt tttagtgggc gtagctaatc ctgcatttgc t             111

<210> SEQ ID NO 14
<211> LENGTH: 37
<212> TYPE: PRT
<213> ORGANISM: Bacillus thuringiensis
<220> FEATURE:
<221> NAME/KEY: MISC_FEATURE
<222> LOCATION: (1)..(37)
<223> OTHER INFORMATION: Amino acid sequence of the secretion signal
      peptide of TIC2421.

<400> SEQUENCE: 14

Met Tyr Thr Asn Asn Lys Met Lys Cys Trp Lys Lys Lys Leu Ala Lys
1               5                   10                  15

Val Ala Pro Ile Cys Val Leu Ser Thr Gly Phe Leu Val Gly Val Ala
                20                  25                  30

Asn Pro Ala Phe Ala
            35
```

```
<210> SEQ ID NO 15
<211> LENGTH: 111
<212> TYPE: DNA
<213> ORGANISM: Bacillus thuringiensis
<220> FEATURE:
<221> NAME/KEY: misc_feature
<222> LOCATION: (1)..(111)
<223> OTHER INFORMATION: DNA sequence encoding the secretion signal
      peptide of TIC3008.

<400> SEQUENCE: 15
atgaaaacta ataaccaaat tagagatcgc aagaaaaaaa tagccaaaat tgtacccatt      60
tgtgtaataa gtacaggatt tttagttgga ctagtgaatc ctgcatttgc a              111

<210> SEQ ID NO 16
<211> LENGTH: 37
<212> TYPE: PRT
<213> ORGANISM: Bacillus thuringiensis
<220> FEATURE:
<221> NAME/KEY: MISC_FEATURE
<222> LOCATION: (1)..(37)
<223> OTHER INFORMATION: Amino acid sequence of Leu Arg Gly Ser Arg Ala Ser Ser Pro Ala Ala Thr Leu Ser Val Arg
    35                  40                  45

Thr Ser Ala Arg Ala Ala Pro Arg Gln Gln His Arg Ala Gln Arg
50                  55                  60

Gly Ala Arg Phe Pro Ser Leu Val Val Cys Ala
65                  70                  75

<210> SEQ ID NO 19
<211> LENGTH: 1203
<212> TYPE: DNA
<213> ORGANISM: Bacillus thuringiensis
<220> FEATURE:
<221> NAME/KEY: misc_feature
<222> LOCATION: (1)..(1203)
<223> OTHER INFORMATION: DNA sequence derived from Bt strain CFB262371
      encoding TIC7055.
<220> FEATURE:
<221> NAME/KEY: misc_feature
<222> LOCATION: (1)..(111)
<223> OTHER INFORMATION: DNA sequence of TIC7055 encoding the secretion
      signal peptide of TIC7055.

<400> SEQUENCE: 19
atgaaaacta ataaccaaat tagagatggc aagaaaaaat tagcacaaat tgtaccgatt      60
tgtgtattaa gtacaggatt tttagttgga ttagtgaatc ctgcatttgc aaaaactacc    120
gaatctcagg tatcctctca acaaattatc catgaccaag tcataaagcc tagatctcta    180
gccacttcta atgataacat taatttggat catattggcg atgacttaaa tcaaagaata    240
tatgacgctg tcaagaatag gccggattta tttgtatacc atcatgtcaa agaagaatcc    300
ggtagaaatg aaaaaattag tgatatggac aaaagcttag caaatggcta tatcgttgta    360
atgaataatc tgaaatatcc cggagttact atcaataacg gatatagtat tgattggaat    420
caacgtgaat acgttggcgg cgatataaag gtgaccggaa acaagataag tgtagacgga    480
ctgcatagtt ttaccttagg gactttccac aatactgaag atatcgaaca aattgctact    540
acacaaaaag aatcctatca aaccaccgat agttttgtat attcaactag taaaggtgtt    600
aaattaggat taaccgaatc cctaaaagca actgcaggtg ttccattaat agtaaatgga    660
gaagaaacga caacactttc aactgagttt tcgtataatc aaacttcttc aaatacagca    720
actaattcac atacaattga atttccatca cagactatta agtgaagcc acacggaact    780 acgatttata ttggtgaagt aaaacagtta aaattctctg gagattattc tggtaccacg    840
aagcttacaa caaagatgt ttctttttccg gtagtcgatt cagaaggtca ttggggagat    900
gttattactg ctccaggtga aaagagcat tttttatata atgtatttaa gtattctggc    960
cactcaatac cggctgatat tcgcttagat gacgaaagta aaacggttgt agtggataat    1020
tcttctattc attttacagg taaattaggt ttcaacatgg aagctacttg gaagttcata    1080
ccagatgacc cacagaaacc aaccgtaacg attcctgatg atgtatatat gaaagaacaa    1140
gcatcaggaa atataagtaa atatattgat caattgataa taaataaaac gcaagctaaa    1200
taa                                                                    1203

<210> SEQ ID NO 20
<211> LENGTH: 400
<212> TYPE: PRT
<213> ORGANISM: Bacillus thuringiensis
<220> FEATURE:
<221> NAME/KEY: MISC_FEATURE
<222> LOCATION: (1)..(400)
<223> OTHER INFORMATION: Amino acid sequence of TIC7055.

```
<220> FEATURE:
<221> NAME/KEY: MISC_FEATURE
<222> LOCATION: (1)..(37)
<223> OTHER INFORMATION: Secretion signal amino acid sequence.

<400> SEQUENCE: 20

Met Lys Thr Asn Asn Gln Ile Arg Asp Gly Lys Lys Leu Ala Gln
1               5                   10                  15

Ile Val Pro Ile Cys Val Leu Ser Thr Gly Phe Leu Val Gly Leu Val
            20                  25                  30

Asn Pro Ala Phe Ala Lys Thr Thr Glu Ser Gln Val Ser Ser Gln Gln
            35                  40                  45

Ile Ile His Asp Gln Val Ile Lys Pro Arg Ser Leu Ala Thr Ser Asn
        50                  55                  60

Asp Asn Ile Asn Leu Asp His Ile Gly Asp Asp Leu Asn Gln Arg Ile
65                  70                  75                  80

Tyr Asp Ala Val Lys Asn Arg Pro Asp Leu Phe Val Tyr His His Val
                85                  90                  95

Lys Glu Glu Ser Gly Arg Asn Glu Lys Ile Ser Asp Met Asp Lys Ser
            100                 105                 110

Leu Ala Asn Gly Tyr Ile Val Val Met Asn Asn Leu Lys Tyr Pro Gly
            115                 120                 125

Val Thr Ile Asn Asn Gly Tyr Ser Ile Asp Trp Asn Gln Arg Glu Tyr
        130                 135                 140

Val Gly Gly Asp Ile Lys Val Thr Gly Lys Gln Asp Ser Val Asp Gly
145                 150                 155                 160

Leu His Ser Phe Thr Leu Gly Thr Phe His Asn Thr Glu Asp Ile Glu
                165                 170                 175

Gln Ile Ala Thr Thr Gln Lys Glu Ser Tyr Gln Thr Thr Asp Ser Phe
            180                 185                 190

Val Tyr Ser Thr Ser Lys Gly Val Lys Leu Gly Leu Thr Glu Ser Leu
        195                 200                 205

Lys Ala Thr Ala Gly Val Pro Leu Ile Val Asn Gly Glu Glu Thr Thr
210                 215                 220

Thr Leu Ser Thr Glu Phe Ser Tyr Asn Gln Thr Ser Ser Asn Thr Ala
225                 230                 235                 240

Thr Asn Ser His Thr Ile Glu Phe Pro Ser Gln Thr Ile Lys Val Lys
                245                 250                 255

Pro His Gly Thr Thr Ile Tyr Ile Gly Glu Val Lys Gln Leu Lys Phe
            260                 265                 270

Ser Gly Asp Tyr Ser Gly Thr Thr Lys Leu Thr Thr Lys Asp Val Ser
        275                 280                 285

Phe Pro Val Val Asp Ser Glu Gly His Trp Gly Asp Val Ile Thr Ala
290                 295                 300

Pro Gly Glu Lys Glu His Phe Leu Tyr Asn Val Phe Lys Tyr Ser Gly
305                 310                 315                 320

His Ser Ile Pro Ala Asp Ile Arg Leu Asp Asp Glu Ser Lys Thr Val
                325                 330                 335

Val Val Asp Asn Ser Ser Ile His Phe Thr Gly Lys Leu Gly Phe Asn
            340                 345                 350

Met Glu Ala Thr Trp Lys Phe Ile Pro Asp Asp Pro Gln Lys Pro Thr
        355                 360                 365

Val Thr Ile Pro Asp Asp Val Tyr Met Lys Glu Gln Ala Ser Gly Asn
    370                 375                 380
```

```
Ile Ser Lys Tyr Ile Asp Gln Leu Ile Ile Asn Lys Thr Gln Ala Lys
385                 390                 395                 400
```

```
<210> SEQ ID NO 21
<211> LENGTH: 111
<212> TYPE: DNA
<213> ORGANISM: Bacillus thuringiensis
<220> FEATURE

```
Thr Gln Lys Glu Ser Tyr Gln Thr Thr Asp Ser Phe Val Tyr Ser Thr
145                 150                 155                 160

Ser Lys Gly Val Lys Leu Gly Leu Thr Glu Ser Leu Lys Ala Thr Ala
                165                 170                 175

Gly Val Pro Leu Ile Val Asn Gly Glu Thr Thr Thr Leu Ser Thr
            180                 185                 190

Glu Phe Ser Tyr Asn Gln Thr Ser Asn Thr Ala Thr Asn Ser His
        195                 200                 205

Thr Ile Glu Phe Pro Ser Gln Thr Ile Lys Val Lys Pro His Gly Thr
    210                 215                 220

Thr Ile Tyr Ile Gly Glu Val Lys Gln Leu Lys Phe Ser Gly Asp Tyr
225                 230                 235                 240

Ser Gly Thr Thr Lys Leu Thr Thr Lys Asp Val Ser Phe Pro Val Val
                245                 250                 255

Asp Ser Glu Gly His Trp Gly Asp Val Ile Thr Ala Pro Gly Glu Lys
            260                 265                 270

Glu His Phe Leu Tyr Asn Val Phe Lys Tyr Ser Gly His Ser Ile Pro
        275                 280                 285

Ala Asp Ile Arg Leu Asp Glu Ser Lys Thr Val Val Asp Asn
290                 295                 300

Ser Ser Ile His Phe Thr Gly Lys Leu Gly Phe Asn Met Glu Ala Thr
305                 310                 315                 320

Trp Lys Phe Ile Pro Asp Pro Gln Lys Pro Thr Val Thr Ile Pro
                325                 330                 335

Asp Asp Val Tyr Met Lys Glu Gln Ala Ser Gly Asn Ile Ser Lys Tyr
            340                 345                 350

Ile Asp Gln Leu Ile Ile Asn Lys Thr Gln Ala Lys
            355                 360
```

<210> SEQ ID NO 24
<211> LENGTH: 439
<212> TYPE: PRT
<213> ORGANISM: Artificial
<220> FEATURE:
<223> OTHER INFORMATION: Amino acid sequence of plastid targeted CTP/mTIC7055.

<400> SEQUENCE: 24

```
Met Ala Ala Leu Ala Thr Ser Gln Leu Ala Thr Thr Arg Ala Gly Phe
1               5                   10                  15

Gly Leu Gly Asp Ala Ser Ser Ser Met Phe Arg Pro Gly Val Gln Gly
                20                  25                  30

Leu Arg Gly Ser Arg Ala Ser Ser Pro Ala Ala Thr Leu Ser Val Arg
            35                  40                  45

Thr Ser Ala Arg Ala Ala Pro Arg Gln Gln His Arg Arg Ala Gln Arg
50                  55                  60

Gly Ala Arg Phe Pro Ser Leu Val Val Cys Ala Met Lys Thr Thr Glu
65                  70                  75                  80

Ser Gln Val Ser Ser Gln Gln Ile Ile His Asp Gln Val Ile Lys Pro
                85                  90                  95

Arg Ser Leu Ala Thr Ser Asn Asp Asn Ile Asn Leu Asp His Ile Gly
            100                 105                 110

Asp Asp Leu Asn Gln Arg Ile Tyr Asp Ala Val Lys Asn Arg Pro Asp
        115                 120                 125

Leu Phe Val Tyr His His Val Lys Glu Glu Ser Gly Arg Asn Glu Lys
    130                 135                 140
```

```
Ile Ser Asp Met Asp Lys Ser Leu Ala Asn Gly Tyr Ile Val Val Met
145                 150                 155                 160

Asn Asn Leu Lys Tyr Pro Gly Val Thr Ile Asn Gly Tyr Ser Ile
            165                 170                 175

Asp Trp Asn Gln Arg Glu Tyr Val Gly Gly Asp Ile Lys Val Thr Gly
        180                 185                 190

Lys Gln Asp Ser Val Asp Gly Leu His Ser Phe Thr Leu Gly Thr Phe
        195                 200                 205

His Asn Thr Glu Asp Ile Glu Gln Ile Ala Thr Thr Gln Lys Glu Ser
        210                 215                 220

Tyr Gln Thr Thr Asp Ser Phe Val Tyr Ser Thr Ser Lys Gly Val Lys
225                 230                 235                 240

Leu Gly Leu Thr Glu Ser Leu Lys Ala Thr Ala Gly Val Pro Leu Ile
                245                 250                 255

Val Asn Gly Glu Glu Thr Thr Thr Leu Ser Thr Glu Phe Ser Tyr Asn
            260                 265                 270

Gln Thr Ser Ser Asn Thr Ala Thr Asn Ser His Thr Ile Glu Phe Pro
        275                 280                 285

Ser Gln Thr Ile Lys Val Lys Pro His Gly Thr Thr Ile Tyr Ile Gly
        290                 295                 300

Glu Val Lys Gln Leu Lys Phe Ser Gly Asp Tyr Ser Gly Thr Thr Lys
305                 310                 315                 320

Leu Thr Thr Lys Asp Val Ser Phe Pro Val Val Asp Ser Glu Gly His
                325                 330                 335

Trp Gly Asp Val Ile Thr Ala Pro Gly Glu Lys Glu His Phe Leu Tyr
            340                 345                 350

Asn Val Phe Lys Tyr Ser Gly His Ser Ile Pro Ala Asp Ile Arg Leu
        355                 360                 365

Asp Asp Glu Ser Lys Thr Val Val Val Asp Asn Ser Ser Ile His Phe
        370                 375                 380

Thr Gly Lys Leu Gly Phe Asn Met Glu Ala Thr Trp Lys Phe Ile Pro
385                 390                 395                 400

Asp Asp Pro Gln Lys Pro Thr Val Thr Ile Pro Asp Asp Val Tyr Met
                405                 410                 415

Lys Glu Gln Ala Ser Gly Asn Ile Ser Lys Tyr Ile Asp Gln Leu Ile
            420                 425                 430

Ile Asn Lys Thr Gln Ala Lys
            435

<210> SEQ ID NO 25
<211> LENGTH: 1215
<212> TYPE: DNA
<213> ORGANISM: Artificial
<220> FEATURE:
<223> OTHER INFORMATION: A recombinant nucleic acid sequence encoding a
      TIC2421 protein with a Histindine tag operably linked to the 3'
      end, referred to as TIC2421_His.

<400> SEQUENCE: 25
atgtatacaa ataataaaat gaagtgttgg aagaaaaaat tagccaaagt tgcaccaatt      60
tgtgtgttaa gtacaggatt tttagtgggc gtagctaatc ctgcatttgc tgctagtaag    120 actcccccaaa ctgttcacgc tcaagcgaaa caatctaatt tatcgactac gtctaatagt    180
aacttagttc atatcggtga tgatttaaat caaagaatcc atgatgctgt gaaaaataaa    240
cccgatttat ttttgtatag atatcttagg gatgatagag gaagaacgaa tgtgcggatg    300
```

```
aatgatatgc ctcaaagtga acacagtggt tataactttg taatgaatag cttacaatac    360
ggaaaagtta cgattaacaa tggatataat atcgattgga atcaaagaga atatgtcggt    420
ggagatatca aggtaacggg taaacaagat agcataggtg gattgcatag ctttacaata    480
ggaacttttc ataacactga agatattgaa caaacggcta ctacgcaaaa agaaacctat    540
caaacaacag atagttttac ctattcaaat agtgagggtg tcaagttagg attgacagaa    600
tctataaaag caactgctgg tgtaccttt gttatagcag gcgaagagac aaccacactc    660
tcaagtgagt tttcatataa tcatacctct tcaaatacat cgacgaactc acatacaatt    720
gaatttccat cgcagactat taaagtcaaa ccgcatggaa ctacacttta cacgggtgag    780
gtaaaacaaa tgaattttc tggagattac tctgggacag tgaaattatc aacaaaggat    840 gtttctttg caataacgga ttcgggaggt cattggggag atattatcgc tgcgccgggt    900
gaagaggagc attttttata taatatattt aaatactccg gtcatccaat tccttcagat    960
attcgtttag atgatgaaaa tagaacggtt gttgttgata attcatccat tcattttaca   1020
ggaaaactag gttttaacat ggaggcaaca tggaaattca tccctgatga tcctaaaaaa   1080
ccaagtgtta caataccaaa tgatgtatat ttaaaagaac aagcttctgg gaatattagc   1140
aagtacattg accaattaat acaaactaaa atgaaatcta tgcatcagca ccaccatcac   1200
gctcaccatc actga                                                    1215
```

<210> SEQ ID NO 26
<211> LENGTH: 404
<212> TYPE: PRT
<213> ORGANISM: Artificial
<220> FEATURE:
<223> OTHER INFORMATION: The amino acid sequence of TIC2421_His.

<400> SEQUENCE: 26

```
Met Tyr Thr Asn Asn Lys Met Lys Cys Trp Lys Lys Lys Leu Ala Lys
1               5                   10                  15

Val Ala Pro Ile Cys Val Leu Ser Thr Gly Phe Leu Val Gly Val Ala
            20                  25                  30

Asn Pro Ala Phe Ala Ala Ser Lys Thr Pro Gln Thr Val His Ala Gln
        35                  40                  45

Ala Lys Gln Ser Asn Leu Ser Thr Thr Ser Asn Ser Asn Leu Val His
    50                  55                  60

Ile Gly Asp Asp Leu Asn Gln Arg Ile His Asp Ala Val Lys Asn Lys
65                  70                  75                  80

Pro Asp Leu Phe Leu Tyr Arg Tyr Leu Arg Asp Asp Arg Gly Arg Thr
                85                  90                  95

Asn Val Arg Met Asn Asp Met Pro Gln Ser Asp Asn Ser Gly Tyr Asn
            100                 105                 110

Phe Val Met Asn Ser Leu Gln Tyr Gly Lys Val Thr Ile Asn Asn Gly
        115                 120                 125

Tyr Asn Ile Asp Trp Asn Gln Arg Glu Tyr Val Gly Gly Asp Ile Lys
    130                 135                 140

Val Thr Gly Lys Gln Asp Ser Ile Gly Gly Leu His Ser Phe Thr Ile
145                 150                 155                 160

Gly Thr Phe His Asn Thr Glu Asp Ile Glu Gln Thr Ala Thr Thr Gln
                165                 170                 175

Lys Glu Thr Tyr Gln Thr Thr Asp Ser Phe Tyr Ser Asn Ser Glu
            180                 185                 190
```

```
Gly Val Lys Leu Gly Leu Thr Glu Ser Ile Lys Ala Thr Ala Gly Val
            195                 200                 205

Pro Phe Val Ile Ala Gly Glu Glu Thr Thr Leu Ser Ser Glu Phe
    210                 215                 220

Ser Tyr Asn His Thr Ser Ser Asn Thr Ser Thr Asn Ser His Thr Ile
225                 230                 235                 240

Glu Phe Pro Ser Gln Thr Ile Lys Val Lys Pro His Gly Thr Thr Leu
                245                 250                 255

Tyr Thr Gly Glu Val Lys Gln Met Asn Phe Ser Gly Asp Tyr Ser Gly
            260                 265                 270

Thr Val Lys Leu Ser Thr Lys Asp Val Ser Phe Ala Ile Thr Asp Ser
        275                 280                 285

Gly Gly His Trp Gly Asp Ile Ile Ala Ala Pro Gly Glu Glu His
    290                 295                 300

Phe Leu Tyr Asn Ile Phe Lys Tyr Ser Gly His Pro Ile Pro Ser Asp
305                 310                 315                 320

Ile Arg Leu Asp Asp Glu Asn Arg Thr Val Val Asp Asn Ser Ser
                325                 330                 335

Ile His Phe Thr Gly Lys Leu Gly Phe Asn Met Glu Ala Thr Trp Lys
            340                 345                 350

Phe Ile Pro Asp Asp Pro Lys Lys Pro Ser Val Thr Ile Pro Asn Asp
        355                 360                 365

Val Tyr Leu Lys Glu Gln Ala Ser Gly Asn Ile Ser Lys Tyr Ile Asp
    370                 375                 380

Gln Leu Ile Gln Thr Lys Met Lys Ser Met His Gln His His His
385                 390                 395                 400

Ala His His His

<210> SEQ ID NO 27
<211> LENGTH: 1227
<212> TYPE: DNA
<213> ORGANISM: Artificial
<220> FEATURE:
<223> OTHER INFORMATION: A recombinant nucleic acid sequence encoding a
      TIC3008 protein with a Histindine tag operably linked to the 3'
      end, referred to as TIC3008_His.

<400> SEQUENCE: 27
atgaaaacta taaccaaat tagagatcgc aagaaaaaaa tagccaaaat tgtacccatt      60
tgtgtaataa gtacaggatt tttagttgga ctagtgaatc ctgcatttgc aaaaactacc   120
gaatctaagc tatcttctca acaaactatc catgaccaag cataaagtc tacatccctg    180 gccacttcta atgacaatat taatttgtat catattggag atgacttaaa tcaagaata    240 tatgacgctg tcaagaatag accagattta tttgtatacc atcatgtcaa aggagaatct   300
ggtagaaatg aaaaaatcag tgatatggac aaaagtttaa caaatggcta tatcgttgta   360
atgaataatc tgaaataccc tggagttact atcaataacg gatataatat tgattggaat   420
caacgtgaat acgttggggg cgatataaag gtgacaggaa acaagatag tgtagacgga   480 ctgcatagtt ttaccttagg aactttccac aatactgaaa atatcgaaca aattgctacg   540
acacaaaaag aatcctatca aaccaccgat agttttacat attcaactag taagggggtt   600
aaattaggat taaccgaatc cctaaaagca actgcaggtg ttccattaat agtaaatgga   660
gaagaaacga caacttttc aactgagttt tcgtataatc aaacttcttc aaatacagca   720
actaattcac atacaattga attcccatca cagactatta agtgaaacc gcacggaact   780
```

-continued

```
acgatttata ttggtgaagt gaaacagtta aaattctctg gagattattc tggtaccaca     840
aagcttacaa cacaagatgt ctcttttccg atagtggatt cagaaggtca ttggggagat     900
gtaattgctg ctccaggtga gaaagaacat tttttatata atatatttaa gtattctggt     960
cactcaatcc cagctgatat tcgcttagat gacgcaagca aaactgttgt ggtggataat    1020
tcttccattc attttacagg taaattaggt ttcaacatgg aagctacttg gaagttcata    1080
ccagatgatc cacaaaaacc agccgtaacg attcctcacg atgtatatat gaaagaacaa    1140
gcatcaggga atataagtaa atatattgat caattgatat taaataaaac gcaagctaaa    1200
caccaccatc acgctcacca tcactga                                        1227
```

<210> SEQ ID NO 28
<211> LENGTH: 408
<212> TYPE: PRT
<213> ORGANISM: Artificial
<220> FEATURE:
<223> OTHER INFORMATION: The amino acid sequence of TIC3008_His.

<400> SEQUENCE: 28

```
Met Lys Thr Asn Asn Gln Ile Arg Asp Arg Lys Lys Ile Ala Lys
1               5                   10                  15

Ile Val Pro Ile Cys Val Ile Ser Thr Gly Phe Leu Val Gly Leu Val
                20                  25                  30

Asn Pro Ala Phe Ala Lys Thr Thr Glu Ser Lys Leu Ser Ser Gln Gln
            35                  40                  45

Thr Ile His Asp Gln Gly Ile Lys Ser Thr Ser Leu Ala Thr Ser Asn
        50                  55                  60

Asp Asn Ile Asn Leu Tyr His Ile Gly Asp Asp Leu Asn Gln Arg Ile
65                  70                  75                  80

Tyr Asp Ala Val Lys Asn Arg Pro Asp Leu Phe Val Tyr His His Val
                85                  90                  95

Lys Gly Glu Ser Gly Arg Asn Glu Lys Ile Ser Asp Met Asp Lys Ser
            100                 105                 110

Leu Thr Asn Gly Tyr Ile Val Val Met Asn Asn Leu Lys Tyr Pro Gly
        115                 120                 125

Val Thr Ile Asn Asn Gly Tyr Asn Ile Asp Trp Asn Gln Arg Glu Tyr
    130                 135                 140

Val Gly Gly Asp Ile Lys Val Thr Gly Lys Gln Asp Ser Val Asp Gly
145                 150                 155                 160

Leu His Ser Phe Thr Leu Gly Thr Phe His Asn Thr Glu Asn Ile Glu
                165                 170                 175

Gln Ile Ala Thr Thr Gln Lys Glu Ser Tyr Gln Thr Thr Asp Ser Phe
            180                 185                 190

Thr Tyr Ser Thr Ser Lys Gly Val Lys Leu Gly Leu Thr Glu Ser Leu
        195                 200                 205

Lys Ala Thr Ala Gly Val Pro Leu Ile Val Asn Gly Glu Glu Thr Thr
    210                 215                 220

Thr Leu Ser Thr Glu Phe Ser Tyr Asn Gln Thr Ser Ser Asn Thr Ala
225                 230                 235                 240

Thr Asn Ser His Thr Ile Glu Phe Pro Ser Gln Thr Ile Lys Val Lys
                245                 250                 255

Pro His Gly Thr Thr Ile Tyr Ile Gly Glu Val Lys Gln Leu Lys Phe
            260                 265                 270

Ser Gly Asp Tyr Ser Gly Thr Thr Lys Leu Thr Thr Gln Asp Val Ser
        275                 280                 285
```

```
Phe Pro Ile Val Asp Ser Glu Gly His Trp Gly Asp Val Ile Ala Ala
    290                 295                 300

Pro Gly Glu Lys Glu His Phe Leu Tyr Asn Ile Phe Lys Tyr Ser Gly
305                 310                 315                 320

His Ser Ile Pro Ala Asp Ile Arg Leu Asp Asp Ala Ser Lys Thr Val
                325                 330                 335

Val Val Asp Asn Ser Ser Ile His Phe Thr Gly Lys Leu Gly Phe Asn
            340                 345                 350

Met Glu Ala Thr Trp Lys Phe Ile Pro Asp Asp Pro Gln Lys Pro Ala
        355                 360                 365

Val Thr Ile Pro His Asp Val Tyr Met Lys Glu Gln Ala Ser Gly Asn
    370                 375                 380

Ile Ser Lys Tyr Ile Asp Gln Leu Ile Leu Asn Lys Thr Gln Ala Lys
385                 390                 395                 400

His His His His Ala His His His
                405
```

<210> SEQ ID NO 29
<211> LENGTH: 1227
<212> TYPE: DNA
<213> ORGANISM: Artificial
<220> FEATURE:
<223> OTHER INFORMATION: A recombinant nucleic acid sequence encoding a
      TIC7055 protein with a Histindine tag operably linked to the 3'
      end, referred to as TIC7055_His.

<400> SEQUENCE: 29

```
atgaaaacta ataaccaaat tagagatggc aagaaaaaat tagcacaaat tgtaccgatt       60
tgtgtattaa gtacaggatt tttagttgga ttagtgaatc ctgcatttgc aaaaactacc      120
gaatctcagg tatcctctca acaaattatc catgaccaag tcataaagcc tagatctcta      180
gccacttcta atgataacat taatttggat catattggcg atgacttaaa tcaaagaata      240
tatgacgctg tcaagaatag gccggattta tttgtatacc atcatgtcaa agaagaatcc      300
ggtagaaatg aaaaaattag tgatatgdac aaaagcttag caaatggcta tatcgttgta      360
atgaataatc tgaaatatcc cggagttact atcaataacg atatagtat tgattggaat       420 caacgtgaat acgttggcgg cgatataaag gtgaccggaa acaagatag tgtagacgga       480 ctgcatagtt ttaccttagg gactttccac aatactgaag atatcgaaca aattgctact      540
acacaaaaag aatcctatca aaccaccgat agttttgtat attcaactag taaaggtgtt      600
aaattaggat taaccgaatc cctaaaagca actgcaggtg ttccattaat agtaaatgga      660
gaagaaacga caacactttc aactgagttt tcgtataatc aaacttcttc aaatacagca      720
actaattcac atacaattga atttccatca cagactatta aagtgaagcc acacggaact      780
acgatttata ttggtgaagt aaaacagtta aaattctctg gagattattc tggtaccacg      840
aagcttacaa caaagatgt ttctttccg gtagtcgatt cagaaggtca ttggggagat       900
gttattactg ctccaggtga aaagagcat tttttatata atgtatttaa gtattctggc       960
cactcaatac cggctgatat tcgcttagat gacgaaagta aaacggttgt agtggataat      1020
tcttctattc attttacagg taattaggt ttcaacatgg aagctacttg gaagttcata      1080
ccagatgacc cacagaaacc aaccgtaacg attcctgatg atgtatatat gaaagaacaa      1140
gcatcaggaa atataagtaa atatattgat caattgataa taaataaaac gcaagctaaa      1200
caccaccatc acgctcacca tcactga                                          1227
```

```
<210> SEQ ID NO 30
<211> LENGTH: 408
<212> TYPE: PRT
<213> ORGANISM: Artificial
<220> FEATURE:
<223> OTHER INFORMATION: The amino acid sequence of TIC7055_His.

<400> SEQUENCE: 30

Met Lys Thr Asn Asn Gln Ile Arg Asp Gly Lys Lys Leu Ala Gln
1               5                   10                  15

Ile Val Pro Ile Cys Val Leu Ser Thr Gly Phe Leu Val Gly Leu Val
            20                  25                  30

Asn Pro Ala Phe Ala Lys Thr Thr Glu Ser Gln Val Ser Ser Gln Gln
            35                  40                  45

Ile Ile His Asp Gln Val Ile Lys Pro Arg Ser Leu Ala Thr Ser Asn
        50                  55                  60

Asp Asn Ile Asn Leu Asp His Ile Gly Asp Asp Leu Asn Gln Arg Ile
65                  70                  75                  80

Tyr Asp Ala Val Lys Asn Arg Pro Asp Leu Phe Val Tyr His His Val
                85                  90                  95

Lys Glu Glu Ser Gly Arg Asn Glu Lys Ile Ser Asp Met Asp Lys Ser
            100                 105                 110

Leu Ala Asn Gly Tyr Ile Val Val Met Asn Asn Leu Lys Tyr Pro Gly
            115                 120                 125

Val Thr Ile Asn Asn Gly Tyr Ser Ile Asp Trp Asn Gln Arg Glu Tyr
        130                 135                 140

Val Gly Gly Asp Ile Lys Val Thr Gly Lys Gln Asp Ser Val Asp Gly
145                 150                 155                 160

Leu His Ser Phe Thr Leu Gly Thr Phe His Asn Thr Glu Asp Ile Glu
                165                 170                 175

Gln Ile Ala Thr Thr Gln Lys Glu Ser Tyr Gln Thr Thr Asp Ser Phe
            180                 185                 190

Val Tyr Ser Thr Ser Lys Gly Val Lys Leu Gly Leu Thr Glu Ser Leu
        195                 200                 205

Lys Ala Thr Ala Gly Val Pro Leu Ile Val Asn Gly Glu Glu Thr Thr
210                 215                 220

Thr Leu Ser Thr Glu Phe Ser Tyr Asn Gln Thr Ser Ser Asn Thr Ala
225                 230                 235                 240

Thr Asn Ser His Thr Ile Glu Phe Pro Ser Gln Thr Ile Lys Val Lys
                245                 250                 255

Pro His Gly Thr Thr Ile Tyr Ile Gly Glu Val Lys Gln Leu Lys Phe
            260                 265                 270

Ser Gly Asp Tyr Ser Gly Thr Thr Lys Leu Thr Thr Lys Asp Val Ser
        275                 280                 285

Phe Pro Val Val Asp Ser Glu Gly His Trp Gly Asp Val Ile Thr Ala
290                 295                 300

Pro Gly Glu Lys Glu His Phe Leu Tyr Asn Val Phe Lys Tyr Ser Gly
305                 310                 315                 320

His Ser Ile Pro Ala Asp Ile Arg Leu Asp Asp Glu Ser Lys Thr Val
                325                 330                 335

Val Val Asp Asn Ser Ser Ile His Phe Thr Gly Lys Leu Gly Phe Asn
            340                 345                 350

Met Glu Ala Thr Trp Lys Phe Ile Pro Asp Asp Pro Gln Lys Pro Thr
        355                 360                 365
```

-continued

```
Val Thr Ile Pro Asp Asp Val Tyr Met Lys Glu Gln Ala Ser Gly Asn
    370                 375                 380

Ile Ser Lys Tyr Ile Asp Gln Leu Ile Ile Asn Lys Thr Gln Ala Lys
385                 390                 395                 400

His His His His Ala His His His
                405
```

UNITED STATES PATENT AND TRADEMARK OFFICE
CERTIFICATE OF CORRECTION

PATENT NO. : 10,036,037 B2
APPLICATION NO. : 15/230112
DATED : July 31, 2018
INVENTOR(S) : David J. Bowen et al.

Page 1 of 1

It is certified that error appears in the above-identified patent and that said Letters Patent is hereby corrected as shown below:

In the Claims

Column 77, Line 15, please delete "wherein:", and insert --wherein--

Column 77, Line 16, please delete "the", and insert --an--

Column 77, Line 59, please delete "speciose", and insert --speciosa--

Column 78, Line 56, please delete "VIP3 A, VIP3 B,", and insert --VIP3A, VIP3B,--

Column 78, Line 57, please delete "AXMI- 100,", and insert --AXMI-100,--

Column 78, Line 59, please delete "AXMI- 184,", and insert --AXMI-184,--

Column 78, Line 62, please delete "AXMI-34,", and insert --AXMI-345,--

Signed and Sealed this
Thirteenth Day of November, 2018

Andrei Iancu
*Director of the United States Patent and Trademark Office*